United States Patent
Tian et al.

(10) Patent No.: US 11,613,584 B1
(45) Date of Patent: Mar. 28, 2023

(54) ANTIBODIES BINDING CD70, PREPARATION AND USE THEREOF

(71) Applicant: IMMUNEONCO BIOPHARMACEUTICALS (SHANGHAI) INC., Shanghai (CN)

(72) Inventors: Wenzhi Tian, Shanghai (CN); Song Li, Shanghai (CN); Dianze Chen, Shanghai (CN); Huiqin Guo, Shanghai (CN)

(73) Assignee: IMMUNEONCO BIOPHARMACEUTICALS (SHANGHAI) INC., Shanghai (CN)

( * ) Notice: Subject to any disclaimer, the term of this patent is extended or adjusted under 35 U.S.C. 154(b) by 0 days.

(21) Appl. No.: 17/685,501

(22) Filed: Mar. 3, 2022

(30) Foreign Application Priority Data

Oct. 13, 2021 (CN) .......................... 202111191860.4

(51) Int. Cl.
| | | |
|---|---|---|
| *C07K 16/28* | (2006.01) | |
| *A61P 35/00* | (2006.01) | |
| *A61K 39/00* | (2006.01) | |

(52) U.S. Cl.
CPC .......... *C07K 16/2875* (2013.01); *A61P 35/00* (2018.01); *A61K 2039/505* (2013.01); *C07K 2317/21* (2013.01); *C07K 2317/565* (2013.01); *C07K 2317/92* (2013.01)

(58) Field of Classification Search
CPC ............ C07K 16/2875; C07K 2317/21; C07K 2317/92; A61P 35/00; A61K 2039/505
See application file for complete search history.

(56) References Cited

U.S. PATENT DOCUMENTS

| | | | |
|---|---|---|---|
| 2012/0294863 A1 | 11/2012 | Law et al. | |
| 2019/0233529 A1* | 8/2019 | Panowski | ............... A61P 35/00 |

FOREIGN PATENT DOCUMENTS

| | | | |
|---|---|---|---|
| CN | 113754769 A | 12/2021 | |
| WO | 2007038637 A2 | 4/2007 | |
| WO | 2012123586 A1 | 9/2012 | |
| WO | 2013043933 A2 | 3/2013 | |
| WO | 2013192360 A1 | 12/2013 | |
| WO | WO-2015032906 A2 * | 3/2015 | ......... C07K 16/2875 |

OTHER PUBLICATIONS

EPO, European search report of EP22155681.6, the counterpart application filed with EPO, dated Jul. 12, 2022.
J. Jacobs et al: "CD70: An emerging target in cancer immunotherapy", Pharmacology & Therapeutics, vol. 155, Nov. 1, 2015 (Nov. 1, 2015), pp. 1-10.

* cited by examiner

*Primary Examiner* — Jeffrey Stucker
*Assistant Examiner* — Jennifer Ann Benavides
(74) *Attorney, Agent, or Firm* — Duane Morris LLP; Thomas J. Kowalski; Deborah L. Lu

(57) ABSTRACT

Disclosed is an antibody that specifically binds CD70, or an antigen binding portion thereof. A nucleic acid molecule encoding the antibody or antigen binding portion thereof, an expression vector and a host cell comprising the nucleic acid molecule, a method for expressing the antibody or antigen binding portion thereof, and a method for treating a disease associated with CD70 signaling using the antibody or antigen binding portion thereof are also provided.

16 Claims, 10 Drawing Sheets

Specification includes a Sequence Listing.

IMM40H

IMM40M

SEQUENCE LISTING

```
<160> NUMBER OF SEQ ID NOS: 23

<210> SEQ ID NO 1
<211> LENGTH: 8
<212> TYPE: PRT
<213> ORGANISM: Artificial Sequence
<220> FEATURE:
<223> OTHER INFORMATION: HV-CDR1 of IMM40C, IMM40H and IMM40M

<400> SEQUENCE: 1

Gly Tyr Thr Phe Thr Asp Ser Ala
1               5

<210> SEQ ID NO 2
<211> LENGTH: 8
<212> TYPE: PRT
<213> ORGANISM: Artificial Sequence
<220> FEATURE:
<223> OTHER INFORMATION: HV-CDR2 of IMM40C, IMM40H and IMM40M

<400> SEQUENCE: 2

Ile Ser Thr Tyr Asp Gly Asp Thr
1               5

<210> SEQ ID NO 3
<211> LENGTH: 13
<212> TYPE: PRT
<213> ORGANISM: Artificial Sequence
<220> FEATURE:
<223> OTHER INFORMATION: HV-CDR3 of IMM40C, IMM40H and IMM40M

<400> SEQUENCE: 3

Ala Arg Arg Gly Tyr Tyr Asp Tyr Asp Trp Phe Pro Tyr
1               5                   10

<210> SEQ ID NO 4
<211> LENGTH: 10
<212> TYPE: PRT
<213> ORGANISM: Artificial Sequence
<220> FEATURE:
<223> OTHER INFORMATION: LV-CDR1 of IMM40C, IMM40H and IMM40M

<400> SEQUENCE: 4
```

```
Lys Ser Val Ser Ala Ser Gly Tyr Ser Phe
1               5                   10

<210> SEQ ID NO 5
<211> LENGTH: 3
<212> TYPE: PRT
<213> ORGANISM: Artificial Sequence
<220> FEATURE:
<223> OTHER INFORMATION: LV-CDR2 of IMM40C, IMM40H and IMM40M

<400> SEQUENCE: 5

Leu Ala Ser
1

<210> SEQ ID NO 6
<211> LENGTH: 9
<212> TYPE: PRT
<213> ORGANISM: Artificial Sequence
<220> FEATURE:
<223> OTHER INFORMATION: LV-CDR3 of IMM40C, IMM40H and IMM40M

<400> SEQUENCE: 6

Gln His Ser Arg Glu Leu Pro Pro Thr
1               5

<210> SEQ ID NO 7
<211> LENGTH: 120
<212> TYPE: PRT
<213> ORGANISM: Artificial Sequence
<220> FEATURE:
<223> OTHER INFORMATION: Heavy chain variable region of IMM40C

<400> SEQUENCE: 7

Gln Val Gln Leu Gln Gln Ser Gly Pro Glu Val Val Arg Pro Gly Val
1               5                   10                  15

Ser Val Lys Ile Ser Cys Lys Gly Ser Gly Tyr Thr Phe Thr Asp Ser
            20                  25                  30

Ala Leu His Trp Val Lys Gln Ser His Ala Lys Ser Leu Glu Trp Ile
        35                  40                  45

Gly Val Ile Ser Thr Tyr Asp Gly Asp Thr Tyr Asn Gln Lys Phe
    50                  55                  60

Lys Gly Lys Ala Thr Met Thr Val Asp Lys Ser Ser Ser Thr Ala Tyr
65                  70                  75                  80

Met Glu Leu Ala Arg Leu Thr Ser Glu Asp Ser Ala Ile Tyr Tyr Cys
                85                  90                  95

Ala Arg Arg Gly Tyr Tyr Asp Tyr Asp Trp Phe Pro Tyr Trp Gly Gln
            100                 105                 110

Gly Thr Leu Val Thr Val Ser Ala
        115                 120

<210> SEQ ID NO 8
<211> LENGTH: 111
<212> TYPE: PRT
<213> ORGANISM: Artificial Sequence
<220> FEATURE:
<223> OTHER INFORMATION: Light chain variable region of IMM40C

<400> SEQUENCE: 8

Asp Ile Val Leu Thr Gln Ser Pro Ala Ser Leu Ala Ile Ser Leu Gly
1               5                   10                  15

Gln Arg Ala Thr Ile Ser Cys Arg Ala Ser Lys Ser Val Ser Ala Ser
            20                  25                  30
```

Gly Tyr Ser Phe Leu His Trp Tyr Gln Gln Lys Pro Gly Gln Pro
            35                  40                  45

Lys Leu Leu Ile Tyr Leu Ala Ser Asn Leu Glu Ser Gly Val Pro Ala
     50                  55                  60

Arg Phe Ser Gly Ser Gly Ser Gly Thr Asp Phe Thr Leu Asn Ile His
 65                  70                  75                  80

Pro Val Glu Glu Glu Asp Ala Ala Thr Phe Tyr Cys Gln His Ser Arg
                 85                  90                  95

Glu Leu Pro Pro Thr Phe Gly Gly Gly Thr Lys Leu Glu Ile Lys
            100                 105                 110

<210> SEQ ID NO 9
<211> LENGTH: 120
<212> TYPE: PRT
<213> ORGANISM: Artificial Sequence
<220> FEATURE:
<223> OTHER INFORMATION: Heavy chain variable region of IMM40H and
      IMM40M

<400> SEQUENCE: 9

Gln Val Gln Leu Val Gln Ser Gly Ala Glu Val Lys Lys Pro Gly Ala
 1               5                  10                  15

Ser Val Lys Val Ser Cys Lys Val Ser Gly Tyr Thr Phe Thr Asp Ser
             20                  25                  30

Ala Leu His Trp Val Arg Gln Ala Pro Gly Lys Gly Leu Glu Trp Met
         35                  40                  45

Gly Val Ile Ser Thr Tyr Asp Gly Asp Thr Tyr Asn Gln Lys Phe
     50                  55                  60

Lys Gly Arg Val Thr Met Thr Glu Asp Thr Ser Thr Asp Thr Ala Tyr
 65                  70                  75                  80

Met Glu Leu Ser Ser Leu Arg Ser Glu Asp Thr Ala Val Tyr Tyr Cys
                 85                  90                  95

Ala Arg Arg Gly Tyr Tyr Asp Tyr Asp Trp Phe Pro Tyr Trp Gly Gln
            100                 105                 110

Gly Thr Leu Val Thr Val Ser Ala
        115                 120

<210> SEQ ID NO 10
<211> LENGTH: 111
<212> TYPE: PRT
<213> ORGANISM: Artificial Sequence
<220> FEATURE:
<223> OTHER INFORMATION: Light chain variable region of IMM40H/IMM40M
<220> FEATURE:
<221> NAME/KEY: misc_feature
<222> LOCATION: (85)..(85)
<223> OTHER INFORMATION: Xaa can be Asn or Glu

<400> SEQUENCE: 10

Asp Ile Val Leu Thr Gln Ser Pro Ala Ser Leu Ala Val Ser Pro Gly
 1               5                  10                  15

Gln Arg Ala Thr Ile Thr Cys Arg Ala Ser Lys Ser Val Ser Ala Ser
             20                  25                  30

Gly Tyr Ser Phe Leu His Trp Tyr Gln Gln Lys Pro Gly Gln Pro Pro
         35                  40                  45

Lys Leu Leu Ile Tyr Leu Ala Ser Asn Leu Glu Ser Gly Val Pro Ala
     50                  55                  60

Arg Phe Ser Gly Ser Gly Ser Gly Thr Asp Phe Thr Leu Thr Ile Asn
 65                  70                  75                  80

Pro Val Glu Ala Xaa Asp Thr Ala Asn Tyr Tyr Cys Gln His Ser Arg
                85                  90                  95

Glu Leu Pro Pro Thr Phe Gly Gly Gly Thr Lys Val Glu Ile Lys
            100                 105                 110

<210> SEQ ID NO 11
<211> LENGTH: 330
<212> TYPE: PRT
<213> ORGANISM: Artificial Sequence
<220> FEATURE:
<223> OTHER INFORMATION: Heavy chain constant region

<400> SEQUENCE: 11

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ala Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Ala Ala Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 12
<211> LENGTH: 107
<212> TYPE: PRT
<213> ORGANISM: Artificial Sequence
<220> FEATURE:
<223> OTHER INFORMATION: Light chain constant region

<400> SEQUENCE: 12

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 13
<211> LENGTH: 1410
<212> TYPE: DNA
<213> ORGANISM: Artificial Sequence
<220> FEATURE:
<223> OTHER INFORMATION: IMM40C's heavy chain

<400> SEQUENCE: 13

| | | |
|---|---|---|
| atgggttgga gctgtatcat cttctttctg gtagcaacag ctacaggtgt gcactcccag | 60 |
| gtccagctgc agcagtctgg gcctgaggtg gtgaggcctg ggtctcagt gaagatttcc | 120 |
| tgcaagggtt ccggctacac attcactgat agtgctttgc actgggtgaa gcagagtcat | 180 |
| gcaaagagtc tagagtggat tggagttatt agtacttacg atggtgatac agactacaac | 240 |
| cagaagttta agggcaaggc cacaatgact gtagacaaat cctccagcac agcctatatg | 300 |
| gaacttgcca gattgacatc tgaggattct gccatctatt actgtgcaag aaggggatac | 360 |
| tatgattacg actggtttcc ttactggggc aagggactc tggtcactgt ctctgcagct | 420 |
| agcaccaagg gcccatcggt cttccccctg gcaccctcct ccaagagcac ctctgggggc | 480 |
| acagcggccc tgggctgcct ggtcaaggac tacttccccg aaccggtgac ggtgtcgtgg | 540 |
| aactcaggcg ccctgaccag cggcgtgcac accttcccgg ctgtcctaca gtcctcagga | 600 |
| ctctactccc tcagcagcgt ggtgaccgtg ccctccagca gcttgggcac ccagacctac | 660 |
| atctgcaacg tgaatcacaa gcccagcaac accaaggtgg acaagagagt gagcccaaa | 720 |
| tcttgtgaca aaactcacac atgcccaccg tgcccagcac ctgaactcct ggggggaccg | 780 |
| tcagtcttcc tcttcccccc aaaacccaag gacaccctca tgatctcccg gacccctgag | 840 |
| gtcacatgcg tggtggtgga cgtgagccac gaagaccctg aggtcaagtt caactggtat | 900 |
| gtggacggcg tggaggtgca taatgccaag acaaagccgc gggaggagca gtacaacgcc | 960 |
| acgtaccgtg tggtcagcgt cctcaccgtc ctgcaccaag actggctgaa tggcaaggag | 1020 |
| tacaagtgca aggtctccaa caaagccctc ccagccccca tcgccgcaac catctccaaa | 1080 |
| gccaaagggc agccccgaga accacaggtg tacaccctgc ccccatcccg ggaggagatg | 1140 |

```
accaagaacc aagtcagcct gacctgcctg gtcaaaggct tctatcccag cgacatcgcc   1200
gtggagtggg agagcaatgg gcagccggag aacaactaca agaccacgcc tcccgtgctg   1260
gactccgacg gctccttctt cctctattcc aagctcaccg tggacaagag caggtggcag   1320
caggggaacg tcttctcatg ctccgtgatg catgaggctc tgcacaacca ctacacgcag   1380
aagagcctct ccctgtctcc gggcaaatga                                    1410

<210> SEQ ID NO 14
<211> LENGTH: 856
<212> TYPE: DNA
<213> ORGANISM: Artificial Sequence
<220> FEATURE:
<223> OTHER INFORMATION: IMM40C's light chain

<400> SEQUENCE: 14
atggagacag acacactcct gttatgggta ctgctgctct gggttccagg ttccactggt     60
gacattgtgc tgacacagtc tcctgcttcc ttagctatat ctctgggggca gagggccacc  120 atctcatgca gggccagcaa aagtgtcagt gcatctggct atagttttct gcactggtac   180
caacagaaac caggacagcc acccaaactc ctcatctatc ttgcatccaa cctcgaatct   240
ggggtccctg ccaggttcag tggcagtggg tctgggacag actttaccct caacatccat   300
cctgtggagg aggaggatgc tgcaacctt tactgtcagc acagtaggga gcttcctccg    360
acgttcggtg gaggcaccaa actggaaatc aaacgtgagt tctagaggat ccatctggga   420
taagcatgct gttttctgtc tgtccctaac atgccctgtg attatccgca acaacacac    480 ccaagggcag aactttgtta cttaaacacc atcctgtttg cttctttcct caggaactgt   540
ggctgcacca tctgtcttca tcttcccgcc atctgatgag cagttgaaat ctggaactgc   600
ctctgttgtg tgcctgctga ataacttcta tcccagagag gccaaagtac agtggaaggt   660
ggataacgcc ctccaatcgg gtaactccca ggagagtgtc acagagcagg acagcaagga   720 cagcaccttac agcctcagca gcaccctgac gctgagcaaa gcagactacg agaaacacaa   780
agtctacgcc tgcgaagtca cccatcaggg cctgagctcg cccgtcacaa agagcttcaa   840 cagggggagag tgttag                                                  856

<210> SEQ ID NO 15
<211> LENGTH: 1410
<212> TYPE: DNA
<213> ORGANISM: Artificial Sequence
<220> FEATURE:
<223> OTHER INFORMATION: IMM40H/IMM40M's heavy chain

<400> SEQUENCE: 15
atgggatggt catgtatcat ccttttctg gtagcaactg caactggagt acattcacaa     60
gtgcagctgg tgcagagcgg cgccgaggtg aagaagcctg gcgcaagcgt gaaggtgagc   120
tgcaaggtga gcggctacac cttcaccgac agcgccctgc actgggtgag acaagcccct   180
ggcaagggcc tggagtggat gggcgtgatc agcacctacg acggcgacac cgactacaat   240
cagaagttca gggcagagt gaccatgacc gaggacacaa gcaccgacac cgcctacatg   300
gagctgagca gcctgagaag cgaggacacc gccgtgtact actgcgctag aagaggctac   360
tacgactacg actggttccc ttactgggggc caaggcaccc tggtgaccgt gagcgccgct   420
agcaccaagg gcccatcggt cttccccctg gcaccctcct ccaagagcac ctctgggggc   480
acagcggccc tgggctgcct ggtcaaggac tacttccccg aaccggtgac ggtgtcgtgg   540
```

```
aactcaggcg ccctgaccag cggcgtgcac accttcccgg ctgtcctaca gtcctcagga    600
ctctactccc tcagcagcgt ggtgaccgtg ccctccagca gcttgggcac ccagacctac    660
atctgcaacg tgaatcacaa gcccagcaac accaaggtgg acaagagagt tgagcccaaa    720
tcttgtgaca aaactcacac atgcccaccg tgcccagcac ctgaactcct ggggggaccg    780
tcagtcttcc tcttcccccc aaaacccaag gacaccctca tgatctcccg gacccctgag    840
gtcacatgcg tggtggtgga cgtgagccac gaagaccctg aggtcaagtt caactggtat    900
gtggacggcg tggaggtgca taatgccaag acaaagccgc gggaggagca gtacaacgcc    960
acgtaccgtg tggtcagcgt cctcaccgtc ctgcaccaag actggctgaa tggcaaggag   1020
tacaagtgca aggtctccaa caaagccctc ccagccccca tcgccgcaac catctccaaa   1080
gccaaagggc agccccgaga accacaggtg tacaccctgc ccccatcccg ggaggagatg   1140
accaagaacc aagtcagcct gacctgcctg gtcaaaggct tctatcccag cgacatcgcc   1200
gtggagtggg agagcaatgg gcagccggag aacaactaca agaccacgcc tcccgtgctg   1260
gactccgacg gctccttctt cctctattcc aagctcaccg tggacaagag caggtggcag   1320
caggggaacg tcttctcatg ctccgtgatg catgaggctc tgcacaacca ctacacgcag   1380
aagagcctct ccctgtctcc gggcaaatga                                    1410

<210> SEQ ID NO 16
<211> LENGTH: 853
<212> TYPE: DNA
<213> ORGANISM: Artificial Sequence
<220> FEATURE:
<223> OTHER INFORMATION: IMM40H/IMM40M's light chain
<220> FEATURE:
<221> NAME/KEY: misc_feature
<222> LOCATION: (310)..(310)
<223> OTHER INFORMATION: n is a or g
<220> FEATURE:
<221> NAME/KEY: misc_feature
<222> LOCATION: (312)..(312)
<223> OTHER INFORMATION: n is c or a

<400> SEQUENCE: 16
atgggatggt catgtatcat cctttttctg gtagcaactg caactggagt acattcagac     60
atcgtgctga cacagagccc tgcaagcctg gccgtgagcc tggacagag agccaccatc    120 acctgcagag caagcaagag cgtgagcgca agcggctaca gcttcctgca ctggtatcag    180
cagaagcctg gacagcctcc taagctgctg atctacctgg caagcaacct ggagagcggc    240
gtgcctgcta gattcagcgg cagcggcagc ggcaccgact tcaccctgac catcaaccct    300
gtggaggccn angacaccgc caactactac tgtcagcaca gcagagagct gcctcctacc    360
ttcggcggcg gcaccaaggt ggagatcaag cgtgagttct agaggatcca tctgggataa    420
gcatgctgtt ttctgtctgt ccctaacatg ccctgtgatt atccgcaaac aacacaccca    480
agggcagaac tttgttactt aaacaccatc ctgtttgctt ctttcctcag gaactgtggc    540
tgcaccatct gtcttcatct tcccgccatc tgatgagcag ttgaaatctg gaactgcctc    600
tgttgtgtgc ctgctgaata acttctatcc cagagaggcc aaagtacagt ggaaggtgga    660
taacgccctc caatcgggta actcccagga gagtgtcaca gagcaggaca gcaaggacag    720
cacctacagc ctcagcagca ccctgacgct gagcaaagca gactacgaga aacacaaagt    780
ctacgcctgc gaagtcaccc atcagggcct gagctcgccc gtcacaaaga gcttcaacag    840
gggagagtgt tag                                                      853
```

```
<210> SEQ ID NO 17
<211> LENGTH: 364
<212> TYPE: PRT
<213> ORGANISM: Artificial Sequence
<220> FEATURE:
<223> OTHER INFORMATION: SIRPalphaD1 mutant-Fc (IMM01)

<400> SEQUENCE: 17
```

| | | | | | | | | | | | | | | | |
|---|---|---|---|---|---|---|---|---|---|---|---|---|---|---|---|
| Glu | Glu | Glu | Leu | Gln | Val | Ile | Gln | Pro | Asp | Lys | Ser | Val | Ser | Val | Ala |
| 1 | | | | 5 | | | | | 10 | | | | | 15 | |
| Ala | Gly | Glu | Ser | Ala | Ile | Leu | His | Cys | Thr | Val | Thr | Ser | Leu | Ile | Pro |
| | | | 20 | | | | | 25 | | | | | 30 | | |
| Val | Gly | Pro | Ile | Gln | Trp | Phe | Arg | Gly | Ala | Gly | Pro | Ala | Arg | Glu | Leu |
| | | 35 | | | | | 40 | | | | | 45 | | | |
| Ile | Tyr | Asn | Gln | Lys | Glu | Gly | His | Phe | Pro | Arg | Val | Thr | Thr | Val | Ser |
| | 50 | | | | | 55 | | | | | 60 | | | | |
| Glu | Ser | Thr | Lys | Arg | Glu | Asn | Met | Asp | Phe | Ser | Ile | Ser | Ile | Ser | Ala |
| 65 | | | | | 70 | | | | | 75 | | | | | 80 |
| Ile | Thr | Pro | Ala | Asp | Ala | Gly | Thr | Tyr | Tyr | Cys | Val | Lys | Phe | Arg | Lys |
| | | | | 85 | | | | | 90 | | | | | 95 | |
| Gly | Ser | Pro | Asp | Thr | Glu | Phe | Lys | Ser | Gly | Ala | Gly | Thr | Glu | Leu | Ser |
| | | | 100 | | | | | 105 | | | | | 110 | | |
| Val | Arg | Ala | Lys | Pro | Ser | Ala | Pro | Val | Val | Ser | Gly | Pro | Ala | Ala | Arg |
| | | 115 | | | | | 120 | | | | | 125 | | | |
| Ala | Thr | Pro | Gln | His | Glu | Pro | Lys | Ser | Cys | Asp | Lys | Thr | His | Thr | Cys |
| | 130 | | | | | 135 | | | | | 140 | | | | |
| Pro | Pro | Cys | Pro | Ala | Pro | Glu | Leu | Leu | Gly | Gly | Pro | Ser | Val | Phe | Leu |
| 145 | | | | | 150 | | | | | 155 | | | | | 160 |
| Phe | Pro | Pro | Lys | Pro | Lys | Asp | Thr | Leu | Met | Ile | Ser | Arg | Thr | Pro | Glu |
| | | | | 165 | | | | | 170 | | | | | 175 | |
| Val | Thr | Cys | Val | Val | Val | Asp | Val | Ser | His | Glu | Asp | Pro | Glu | Val | Lys |
| | | | 180 | | | | | 185 | | | | | 190 | | |
| Phe | Asn | Trp | Tyr | Val | Asp | Gly | Val | Glu | Val | His | Asn | Ala | Lys | Thr | Lys |
| | | 195 | | | | | 200 | | | | | 205 | | | |
| Pro | Arg | Glu | Glu | Gln | Tyr | Asn | Ser | Thr | Tyr | Arg | Val | Val | Ser | Val | Leu |
| | 210 | | | | | 215 | | | | | 220 | | | | |
| Thr | Val | Leu | His | Gln | Asp | Trp | Leu | Asn | Gly | Lys | Glu | Tyr | Lys | Cys | Lys |
| 225 | | | | | 230 | | | | | 235 | | | | | 240 |
| Val | Ser | Asn | Lys | Ala | Leu | Pro | Ala | Pro | Ile | Glu | Lys | Thr | Ile | Ser | Lys |
| | | | | 245 | | | | | 250 | | | | | 255 | |
| Ala | Lys | Gly | Gln | Pro | Arg | Glu | Pro | Gln | Val | Tyr | Thr | Leu | Pro | Pro | Ser |
| | | | 260 | | | | | 265 | | | | | 270 | | |
| Arg | Asp | Glu | Leu | Thr | Lys | Asn | Gln | Val | Ser | Leu | Thr | Cys | Leu | Val | Lys |
| | | 275 | | | | | 280 | | | | | 285 | | | |
| Gly | Phe | Tyr | Pro | Ser | Asp | Ile | Ala | Val | Glu | Trp | Glu | Ser | Asn | Gly | Gln |
| | 290 | | | | | 295 | | | | | 300 | | | | |
| Pro | Glu | Asn | Asn | Tyr | Lys | Thr | Thr | Pro | Pro | Val | Leu | Asp | Ser | Asp | Gly |
| 305 | | | | | 310 | | | | | 315 | | | | | 320 |
| Ser | Phe | Phe | Leu | Tyr | Ser | Lys | Leu | Thr | Val | Asp | Lys | Ser | Arg | Trp | Gln |
| | | | | 325 | | | | | 330 | | | | | 335 | |
| Gln | Gly | Asn | Val | Phe | Ser | Cys | Ser | Val | Met | His | Glu | Ala | Leu | His | Asn |
| | | | 340 | | | | | 345 | | | | | 350 | | |
| His | Tyr | Thr | Gln | Lys | Ser | Leu | Ser | Leu | Ser | Pro | Gly | | | | |
| | | 355 | | | | | 360 | | | | | | | | |

```
<210> SEQ ID NO 18
<211> LENGTH: 57
<212> TYPE: DNA
<213> ORGANISM: Artificial Sequence
<220> FEATURE:
<223> OTHER INFORMATION: Signal peptide of murine IgG1 heavy chain

<400> SEQUENCE: 18
atgggatggt catgtatcat ccttttttctg gtagcaactg caactggagt acattca        57

<210> SEQ ID NO 19
<211> LENGTH: 9
<212> TYPE: DNA
<213> ORGANISM: Artificial Sequence
<220> FEATURE:
<223> OTHER INFORMATION: Kozak

<400> SEQUENCE: 19 gccgccacc        9

<210> SEQ ID NO 20
<211> LENGTH: 471
<212> TYPE: PRT
<213> ORGANISM: Artificial Sequence
<220> FEATURE:
<223> OTHER INFORMATION: Cusatuzumab's heavy chain

<400> SEQUENCE: 20
```

Met Gly Trp Ser Cys Ile Ile Leu Phe Leu Val Ala Thr Ala Thr Gly
1               5                   10                  15

Val His Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Val Tyr Tyr Met Asn Trp Val Arg Gln Ala Pro Gly Lys Gly Leu
    50                  55                  60

Glu Trp Val Ser Asp Ile Asn Asn Glu Gly Gly Thr Thr Tyr Tyr Ala
65                  70                  75                  80

Asp Ser Val Lys Gly Arg Phe Thr Ile Ser Arg Asp Asn Ser Lys Asn
                85                  90                  95

Ser Leu Tyr Leu Gln Met Asn Ser Leu Arg Ala Glu Asp Thr Ala Val
            100                 105                 110

Tyr Tyr Cys Ala Arg Asp Ala Gly Tyr Ser Asn His Val Pro Ile Phe
        115                 120                 125

Asp Ser Trp Gly Gln Gly Thr Leu Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Lys Val Glu
225                 230                 235                 240

Pro Lys Ser Cys Asp Lys Thr His Thr Cys Pro Pro Cys Pro Ala Pro

```
                245                 250                 255
Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Asp Glu Leu Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly Lys
465                 470

<210> SEQ ID NO 21
<211> LENGTH: 235
<212> TYPE: PRT
<213> ORGANISM: Artificial Sequence
<220> FEATURE:
<223> OTHER INFORMATION: Cusatuzumab's light chain

<400> SEQUENCE: 21

Met Gly Trp Ser Cys Ile Ile Leu Phe Leu Val Ala Thr Ala Thr Gly
1               5                   10                  15

Val His Ser Gln Ala Val Val Thr Gln Glu Pro Ser Leu Thr Val Ser
            20                  25                  30

Pro Gly Gly Thr Val Thr Leu Thr Cys Gly Leu Lys Ser Gly Ser Val
        35                  40                  45

Thr Ser Asp Asn Phe Pro Thr Trp Tyr Gln Gln Thr Pro Gly Gln Ala
    50                  55                  60

Pro Arg Leu Leu Ile Tyr Asn Thr Asn Thr Arg His Ser Gly Val Pro
65                  70                  75                  80

Asp Arg Phe Ser Gly Ser Ile Leu Gly Asn Lys Ala Ala Leu Thr Ile
                85                  90                  95

Thr Gly Ala Gln Ala Asp Asp Glu Ala Glu Tyr Phe Cys Ala Leu Phe
            100                 105                 110

Ile Ser Asn Pro Ser Val Glu Phe Gly Gly Gly Thr Gln Leu Thr Val
        115                 120                 125

Leu Gly Gln Pro Lys Ala Ala Pro Ser Val Thr Leu Phe Pro Pro Ser
```

```
            130                 135                 140
Ser Glu Glu Leu Gln Ala Asn Lys Ala Thr Leu Val Cys Leu Ile Ser
145                 150                 155                 160

Asp Phe Tyr Pro Gly Ala Val Thr Val Ala Trp Lys Ala Asp Ser Ser
                165                 170                 175

Pro Val Lys Ala Gly Val Glu Thr Thr Thr Pro Ser Lys Gln Ser Asn
                180                 185                 190

Asn Lys Tyr Ala Ala Ser Ser Tyr Leu Ser Leu Thr Pro Glu Gln Trp
                195                 200                 205

Lys Ser His Arg Ser Tyr Ser Cys Gln Val Thr His Glu Gly Ser Thr
                210                 215                 220

Val Glu Lys Thr Val Ala Pro Thr Glu Cys Ser
225                 230                 235

<210> SEQ ID NO 22
<211> LENGTH: 406
<212> TYPE: PRT
<213> ORGANISM: Artificial Sequence
<220> FEATURE:
<223> OTHER INFORMATION: CD27(ECD)-Fc

<400> SEQUENCE: 22

Ala Thr Pro Ala Pro Lys Ser Cys Pro Glu Arg His Tyr Trp Ala Gln
1               5                   10                  15

Gly Lys Leu Cys Cys Gln Met Cys Glu Pro Gly Thr Phe Leu Val Lys
                20                  25                  30

Asp Cys Asp Gln His Arg Lys Ala Ala Gln Cys Asp Pro Cys Ile Pro
            35                  40                  45

Gly Val Ser Phe Ser Pro Asp His His Thr Arg Pro His Cys Glu Ser
        50                  55                  60

Cys Arg His Cys Asn Ser Gly Leu Leu Val Arg Asn Cys Thr Ile Thr
65                  70                  75                  80

Ala Asn Ala Glu Cys Ala Cys Arg Asn Gly Trp Gln Cys Arg Asp Lys
                85                  90                  95

Glu Cys Thr Glu Cys Asp Pro Leu Pro Asn Pro Ser Leu Thr Ala Arg
            100                 105                 110

Ser Ser Gln Ala Leu Ser Pro His Pro Gln Pro Thr His Leu Pro Tyr
        115                 120                 125

Val Ser Glu Met Leu Glu Ala Arg Thr Ala Gly His Met Gln Thr Leu
130                 135                 140

Ala Asp Phe Arg Gln Leu Pro Ala Arg Thr Leu Ser Thr His Trp Pro
145                 150                 155                 160

Pro Gln Arg Ser Leu Cys Ser Ser Asp Phe Ile Arg Glu Phe Glu Pro
                165                 170                 175

Lys Ser Cys Asp Lys Thr His Thr Cys Pro Pro Cys Pro Ala Pro Glu
                180                 185                 190

Leu Leu Gly Gly Pro Ser Val Phe Leu Phe Pro Pro Lys Pro Lys Asp
                195                 200                 205

Thr Leu Met Ile Ser Arg Thr Pro Glu Val Thr Cys Val Val Val Asp
                210                 215                 220

Val Ser His Glu Asp Pro Glu Val Lys Phe Asn Trp Tyr Val Asp Gly
225                 230                 235                 240

Val Glu Val His Asn Ala Lys Thr Lys Pro Arg Glu Glu Gln Tyr Asn
                245                 250                 255

Ser Thr Tyr Arg Val Val Ser Val Leu Thr Val Leu His Gln Asp Trp
```

```
                260                 265                 270
Leu Asn Gly Lys Glu Tyr Lys Cys Lys Val Ser Asn Lys Ala Leu Pro
            275                 280                 285

Ala Pro Ile Glu Lys Thr Ile Ser Lys Ala Lys Gly Gln Pro Arg Glu
        290                 295                 300

Pro Gln Val Tyr Thr Leu Pro Pro Ser Arg Asp Glu Leu Thr Lys Asn
305                 310                 315                 320

Gln Val Ser Leu Thr Cys Leu Val Lys Gly Phe Tyr Pro Ser Asp Ile
                325                 330                 335

Ala Val Glu Trp Glu Ser Asn Gly Gln Pro Glu Asn Asn Tyr Lys Thr
            340                 345                 350

Thr Pro Pro Val Leu Asp Ser Asp Gly Ser Phe Phe Leu Tyr Ser Lys
        355                 360                 365

Leu Thr Val Asp Lys Ser Arg Trp Gln Gln Gly Asn Val Phe Ser Cys
    370                 375                 380

Ser Val Met His Glu Ala Leu His Asn His Tyr Thr Gln Lys Ser Leu
385                 390                 395                 400

Ser Leu Ser Pro Gly Lys
                405

<210> SEQ ID NO 23
<211> LENGTH: 397
<212> TYPE: PRT
<213> ORGANISM: Artificial Sequence
<220> FEATURE:
<223> OTHER INFORMATION: CD27-CAR

<400> SEQUENCE: 23

Ala Thr Pro Ala Pro Lys Ser Cys Pro Glu Arg His Tyr Trp Ala Gln
1               5                   10                  15

Gly Lys Leu Cys Cys Gln Met Cys Glu Pro Gly Thr Phe Leu Val Lys
            20                  25                  30

Asp Cys Asp Gln His Arg Lys Ala Ala Gln Cys Asp Pro Cys Ile Pro
        35                  40                  45

Gly Val Ser Phe Ser Pro Asp His His Thr Arg Pro His Cys Glu Ser
    50                  55                  60

Cys Arg His Cys Asn Ser Gly Leu Leu Val Arg Asn Cys Thr Ile Thr
65                  70                  75                  80

Ala Asn Ala Glu Cys Ala Cys Arg Asn Gly Trp Gln Cys Arg Asp Lys
                85                  90                  95

Glu Cys Thr Glu Cys Asp Pro Leu Pro Asn Pro Ser Leu Thr Ala Arg
            100                 105                 110

Ser Ser Gln Ala Leu Ser Pro His Pro Gln Pro Thr His Leu Pro Tyr
        115                 120                 125

Val Ser Glu Met Leu Glu Ala Arg Thr Ala Gly His Met Gln Thr Leu
    130                 135                 140

Ala Asp Phe Arg Gln Leu Pro Ala Arg Thr Leu Ser Thr His Trp Pro
145                 150                 155                 160

Pro Gln Arg Ser Leu Cys Ser Ser Asp Phe Ile Arg Thr Thr Thr Pro
                165                 170                 175

Ala Pro Arg Pro Pro Thr Pro Ala Pro Thr Ile Ala Ser Gln Pro Leu
            180                 185                 190

Ser Leu Arg Pro Glu Ala Cys Arg Pro Ala Ala Gly Gly Ala Val His
        195                 200                 205

Thr Arg Gly Leu Asp Phe Ala Cys Asp Phe Trp Val Leu Val Val Val
```

-continued

```
                    210                 215                 220
Gly Gly Val Leu Ala Cys Tyr Ser Leu Leu Val Thr Val Ala Phe Ile
225                     230                 235                 240

Ile Phe Trp Val Arg Ser Lys Arg Ser Arg Leu Leu His Ser Asp Tyr
                245                 250                 255

Met Asn Met Thr Pro Arg Arg Pro Gly Pro Thr Arg Lys His Tyr Gln
            260                 265                 270

Pro Tyr Ala Pro Pro Arg Asp Phe Ala Ala Tyr Arg Ser Arg Val Lys
            275                 280                 285

Phe Ser Arg Ser Ala Glu Pro Pro Ala Tyr Gln Gln Gly Gln Asn Gln
        290                 295                 300

Leu Tyr Asn Glu Leu Asn Leu Gly Arg Arg Glu Glu Tyr Asp Val Leu
305                 310                 315                 320

Asp Lys Arg Arg Gly Arg Asp Pro Glu Met Gly Gly Lys Pro Arg Arg
                325                 330                 335

Lys Asn Pro Gln Glu Gly Leu Tyr Asn Glu Leu Gln Lys Asp Lys Met
                340                 345                 350

Ala Glu Ala Tyr Ser Glu Ile Gly Met Lys Gly Glu Arg Arg Arg Gly
            355                 360                 365

Lys Gly His Asp Gly Leu Tyr Gln Gly Leu Ser Thr Ala Thr Lys Asp
        370                 375                 380

Thr Tyr Asp Ala Leu His Met Gln Ala Leu Pro Pro Arg
385                 390                 395
```

ANTIBODIES BINDING CD70, PREPARATION AND USE THEREOF

RELATED APPLICATIONS AND INCORPORATION BY REFERENCE

This application claims priority to Chinese Patent Application No. 202111191860.4 filed on Oct. 13, 2021.

The foregoing application, and all documents cited therein or during its prosecution ("appln cited documents") and all documents cited or referenced herein (including without limitation all literature documents, patents, published patent applications cited herein) ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference. Any Genbank sequences mentioned in this disclosure are incorporated by reference with the Genbank sequence to be that of the earliest effective filing date of this disclosure.

SEQUENCE STATEMENT

The instant application contains a Sequence Listing which has been submitted electronically and is hereby incorporated by reference in its entirety. Said ASCII copy was created Feb. 6, 2022, and revised Apr. 28, 2022, is named 55525_00059SubstituteSL.txt and is 33,656 bytes in size.

FIELD OF THE INVENTION

The application relates to a monoclonal antibody or an antigen binding portion thereof that specifically binds CD70, and the preparation and use thereof, especially the use in tumor therapies.

BACKGROUND OF THE INVENTION

Cancer cells have developed several mechanisms to evade hosts' immune surveillance, including: 1) to highly express CD70 proteins, which may bind to CD27s on immune cells to induce T cell apoptosis/exhaustion and to increase Treg cell population; 2) to promote detachment of MICA/MICB from cancer cell membranes, which bind to NKG2D proteins on natural killer (NK) cell surfaces, blocking MICA/MICB$^+$ cancer cell killing by NK cells; and 3) to express a high level of CD47s, which bind to the signal regulatory protein alpha (SIRPα) on macrophage surfaces, inducing inhibitory signals that inhibit phagocytosis of cancer cells by macrophages. It can be seen that the cancer cells are quite "smart" and reproduce quickly depending on their developed evasion mechanisms. Accordingly, development of effective anti-cancer drugs for killing the cancer cells may focus on targeting these mechanisms.

CD70 and CD27

CD70, a type II transmembrane protein, is a member of the tumor necrosis factor superfamily (B. F. Israel et al., 2005). It is mainly expressed on highly activated lymphocytes and dendritic cells, and its expression was also found on antigen presenting cells. CD70 may bind CD27, a receptor expressed on mature T cells, memory B cells, germinal center B cells, and natural killing (NK) cells. The CD70-CD27 interaction plays an important role in lymphocyte activation and immune response maintenance. For example, the CD70-CD27 signaling may trigger proliferation of CD4$^+$ T cells and CD8$^+$ T cells, and secretion of cytokines. CD70-CD27 interaction may also promote B cell activation, proliferation and differentiation, germinal center formation, and antibody release.

CD70 expressions have been found on many tumor cells, including the cells of renal cell carcinoma, nasopharyngeal carcinoma (A. Agathanggelou et al., 1995), cancers induced by Epstein-Barr virus (EBV$^+$ cancer), Hodgkin lymphoma (HL) (H. J. Gruss et al., 1996), non-Hodgkin lymphoma (NHL), diffuse large B cell lymphoma, follicular lymphoma, B lymphocytic leukemia, Burkitt lymphoma (S. M. Lens et al., 1999), multiple myeloma (J. A. McEarchern et al., 2008), Waldenstrom macroglobulinemia, thymic carcinoma (T. Hishima et al., 2000), renal cell carcinoma (C. L. Law et al., 2006), glioblastoma (J. Wischhusen et al., 2002), brain cancer (J. Held-Feindt et al., 2002), osteosarcoma (J. H. Pahl et al., 2015), melanoma (C. Pich et al., 2016), and ovarian cancer (S. Aggarwal et al., 2008). Tumors may make use of the CD70s expressed on their surfaces to induce T cell apoptosis and exhaustion, and to increase the amount/level of Treg cells (Julie Jacobs et al., 2018). Further, the CD70-CD27 signaling in the acute myelocytic leukemia (AML) cells was reported to initiate stem cell gene expression programs, and promote symmetric cell division and cell proliferation (C. Riether et al., 2017).

In addition to tumor cell surfaces, CD70s are also expressed on tumor microenvironments in e.g., original or metastatic non-small cell lung cancer (NSCLC) (J. Jacobs et al., 2015). Further, the CD70 levels are associated with poor prognosis in patients with B cell lymphoma, renal cell carcinoma, and breast cancer. All these make CD70 a promising target for tumor treatment. Cusatuzumab, an anti-CD70 antibody, successfully eliminated CD70$^+$ leukemia stem cells (LSC), in vitro and in xenotransplantation experiments (C. Riether et al., 2020). CD70-CD27 blockade by antibodies also inhibited AML cell growth (C. Riether et al., 2017, supra). Antibodies targeting CD70-CD27 signaling are under clinical trails for treatment of e.g., squamous cell carcinoma of the head and neck, ovarian carcinoma, colorectal cancer, renal cell carcinoma, glioblastoma multiforme, B-cell malignancy, HL, chronic lymphocytic leukemia, mantle cell lymphoma, marginal zone B cell lymphoma, any T cell malignancy, melanoma, prostate adenocarcinoma, colorectal adenocarcinoma, non-small cell lung cancer, Burkett's lymphoma, lymphoma of the central nervous system, breast carcinoma, and the like (Lutfi F et al., 2021).

Studies have also shown CD70 overexpression is involved in arthritis, inflammatory bowel disease, and lupus (Bobby Kwanghoon Han et al., 2015). Blocking CD27-CD70 pathway by anti-CD70 antibodies ameliorated joint disease in arthritis, and suppressed colitis.

More anti-CD70 antibodies with superior characteristics are needed.

Citation or identification of any document in this application is not an admission that such a document is available as prior art to the present disclosure.

SUMMARY OF THE INVENTION

The present application discloses a novel anti-CD70 antibody or an antigen binding portion thereof, which may bind CD70$^+$ cells, block CD70-CD27 binding/interaction, and induce antibody dependent cell mediated cytotoxicity (ADCC), antibody dependent cellular phagocytosis (ADCP) and/or complement dependent cytotoxicity (CDC) against $CD70^+$ cells, with comparable, if not higher, activity/capability compared to the prior art anti-CD70 antibodies such as cusatuzumab. The antibody or antigen binding portion thereof of the disclosure also showed potent in vivo anti-tumor effects.

Specifically, in an aspect, the present application discloses an isolated monoclonal antibody or an antigen binding portion thereof, that binds CD70, that may comprise i) a heavy chain variable region that may comprise a heavy chain variable region CDR1 (VH-CDR1), a VH-CDR2 and a VH-CDR3, wherein the VH-CDR1, the VH-CDR2 and the VH-CDR3 may comprise amino acid sequences having at least 80%, 81%, 82%, 83%, 84%, 85%, 86%, 87%, 88%, 89%, 90%, 91%, 92%, 93%, 94%, 95%, 96%, 97%, 98%, 99% or 100% identity to SEQ ID NOs: 1, 2 and 3, respectively; and/or ii) a light chain variable region that may comprise a light chain variable region CDR1 (VL-CDR1), a VL-CDR2 and a VL-CDR3, wherein the VL-CDR1, the VL-CDR2 and the VL-CDR3 may comprise amino acid sequences having at least 80%, 81%, 82%, 83%, 84%, 85%, 86%, 87%, 88%, 89%, 90%, 91%, 92%, 93%, 94%, 95%, 96%, 97%, 98%, 99% or 100% identity to SEQ ID NOs: 4, 5 and 6, respectively.

The heavy chain variable region of the disclosure may comprise an amino acid sequence having at least 80%, 81%, 82%, 83%, 84%, 85%, 86%, 87%, 88%, 89%, 90%, 91%, 92%, 93%, 94%, 95%, 96%, 97%, 98%, 99% or 100% identity to SEQ ID NOs: 7 or 9.

The light chain variable region of the disclosure may comprise an amino acid sequence having at least 80%, 81%, 82%, 83%, 84%, 85%, 86%, 87%, 88%, 89%, 90%, 91%, 92%, 93%, 94%, 95%, 96%, 97%, 98%, 99% or 100% identity to SEQ ID NOs: 8 or 10 (X=N or X=E).

The isolated monoclonal antibody or antigen-binding portion thereof of the disclosure may comprise a heavy chain variable region and a light chain variable region which may comprise amino acid sequences having at least 80%, 81%, 82%, 83%, 84%, 85%, 86%, 87%, 88%, 89%, 90%, 91%, 92%, 93%, 94%, 95%, 96%, 97%, 98%, 99% or 100% identity to (1) SEQ ID NOs: 7 and 8, respectively; (2) SEQ ID NOs: 9 and 10 (X=N), respectively; or (3) SEQ ID NOs: 9 and 10 (X=E), respectively.

The isolated monoclonal antibody or antigen binding portion thereof of the disclosure may comprise a heavy chain constant region and/or a light chain constant region. The heavy chain constant region may be an IgG1, IgG2, IgG3 or IgG4 heavy chain constant region, or a functional fragment thereof, that has or has been engineered to have FcR and/or complement system protein (such as C1q) binding affinity. In certain embodiments, the heavy chain constant region may be human IgG1 heavy chain constant region, comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, 99% or 100% identity to e.g., SEQ ID NO: 11. The light chain constant region may be kappa light chain constant region, such as human kappa light chain constant region, comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, 99% or 100% identity to e.g., SEQ ID NO: 12. The N terminus of the heavy chain constant region is linked to the C terminus of the heavy chain variable region, and the N terminus of the light chain constant region is linked to the C terminus of the light chain variable region.

In certain embodiments, the antibody of the disclosure may be an IgG antibody, comprising or consisting of two heavy chains and two light chains connected by disulfide bonds, wherein each heavy chain may comprise the heavy chain constant region, heavy chain variable region and/or CDR sequences mentioned above, and each light chain may comprise the light chain constant region, light chain variable region and/or CDR sequences mentioned above.

The antibody or antigen binding portion thereof of the disclosure may be mouse, chimeric, human or humanized.

The antibody or antigen binding portion thereof of the disclosure may bind CD70, block CD70-CD27 binding/interaction, induce ADCC, ADCP and/or CDC against $CD70^+$ cells, and show potent in vivo anti-tumor effects.

The disclosure also provides an immunoconjugate comprising the antibody or the antigen binding portion thereof, linked to a therapeutic agent such as a cytotoxin or an anti-cancer agent. The disclosure also provides a bispecific molecule comprising the antibody or the antigen-binding portion thereof of the disclosure, linked to a second functional moiety (e.g., a second antibody) having a different binding specificity than the antibody or the antigen-binding portion thereof of the disclosure. In another aspect, the antibody or the antigen-binding portion thereof of the present disclosure can be made into part of a chimeric antigen receptor (CAR) or a T cell receptor (TCR). The disclosure further provides an immune cell with the CAR or TCR of the disclosure, such as a T cell and a NK cell.

The disclosure further provides a nucleic acid molecule encoding the antibody or antigen-binding portion thereof of the disclosure, as well as an expression vector comprising such a nucleic acid molecule and a host cell comprising such an expression vector. A method for preparing the anti-CD70 antibody or antigen binding portion thereof using the host cell of the disclosure is provided, comprising steps of (i) expressing the antibody or antigen binding portion thereof in the host cell, and (ii) isolating the antibody or antigen binding portion thereof from the host cell or its cell culture.

The disclosure provides a pharmaceutical composition comprising the antibody or antigen binding portion thereof, the immunoconjugate, the bispecific molecule, the immune cell, the nucleic acid molecule, the expression vector, or the host cell of the disclosure, and a pharmaceutically acceptable carrier. The pharmaceutical composition of the disclosure may further comprise an anti-tumor agent such as a SIRPalphaD1-Fc fusion protein, or an anti-inflammatory agent.

In another aspect, the disclosure provides a method for treating or alleviating a disease associated with CD70 overexpression or CD70-CD27 signaling in a subject in need thereof, comprising administering to the subject a therapeutically effective amount of the pharmaceutical composition of the disclosure.

The disease may be a cancer. The cancer may be a solid cancer or a hematological cancer, including, but not limited to, kidney cancer, myelodysplastic syndromes, cutaneous T-cell lymphomas, nasopharyngeal carcinoma, Epstein-Barr virus induced cancer, Hodgkin lymphoma (HL), non-Hodgkin lymphoma (NHL), diffuse large B cell lymphoma, follicular lymphoma, B lymphocytic leukemia, Burkitt lymphoma, multiple myeloma, Waldenstrom macroglobulinemia, thymic carcinoma, glioblastoma, brain cancer, osteosarcoma, melanoma, ovarian cancer, renal cell carcinoma, breast cancer, squamous cell carcinoma of the head and neck, colorectal cancer, mantle cell lymphoma, prostate adenocarcinoma, colorectal adenocarcinoma, lymphoma of the central nervous system, or non-small cell lung cancer. In certain embodiments, the pharmaceutical composition of the disclosure may be administered with at least one anti-tumor agent, such a protein targeting CD47. The protein targeting CD47 may be a SIRPalpha-Fc fusion protein having at least 80%, 81%, 82%, 83%, 84%, 85%, 86%, 87%, 88%, 89%, 90%, 91%, 92%, 93%, 94%, 95%, 96%, 97%, 98%, 99% or 100% identity to SEQ ID NO.: 17. It contains an N→A mutation at position 80 of SEQ ID NO: 17 to remove a glycosylation site.

In certain embodiments, the disease may be an inflammatory disease. In certain embodiments, the inflammatory disease may be an autoimmune disease. In certain embodiments, the inflammatory disease may be arthritis, inflammatory bowel disease, or lupus.

The antibody or antigen binding portion thereof of the disclosure may also be used for in vitro detection of CD70 proteins, and amelioration of allogeneic cell transplantation.

Other features and advantages of the instant disclosure will be apparent from the following detailed description and examples which should not be construed as limiting. The contents of all references, GenBank entries, patents and published patent applications cited throughout this application are expressly incorporated herein by reference.

Accordingly, it is an object of the application not to encompass within the application any previously known product, process of making the product, or method of using the product such that Applicants reserve the right and hereby disclose a disclaimer of any previously known product, process, or method. It is further noted that the application does not intend to encompass within the scope of the application any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the application to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved. Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the application.

DESCRIPTION OF THE DRAWINGS

The following detailed description, given by way of example, but not intended to limit the application solely to the specific embodiments described, may best be understood in conjunction with the accompanying drawings.

DETAILED DESCRIPTION OF THE APPLICATION

Figure 1:
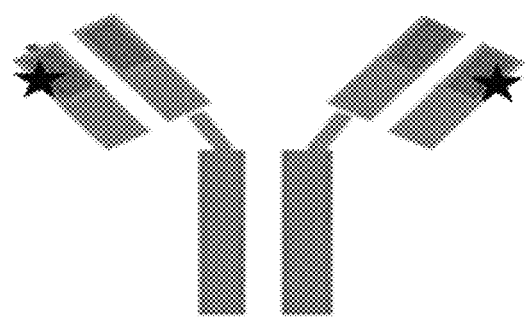
FIG. 1 is a schematic diagram of structures of IMM40H and IMM40M, the anti-CD70 proteins of the disclosure. IMM40H is an IgG antibody, comprising a humanized heavy chain variable region, a heavy chain constant region, a humanized light chain variable region and a light chain constant region, respectively having the amino acid sequences set forth in SEQ ID NOs: 9, 11, 10 (X=N) and 12. IMM40M is similar to IMM40H, but comprises a N85E mutation at the light chain variable region which removes the glycosylation sites represented by *.
Figure 1:
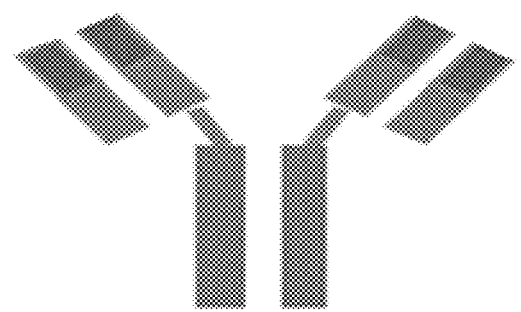

To ensure that the present disclosure may be more readily understood, certain terms are first defined. Additional definitions are set forth throughout the detailed description.

The term "CD70" refers to cluster of differentiation 70. The term "CD70" comprises variants, isoforms, homologs, orthologs and paralogs.

The term "antibody" as referred to herein includes whole antibodies of e.g., IgG, IgA, IgD, IgE and IgM, and any antigen binding fragment (i.e., "antigen-binding portion") or single chains thereof. Whole antibodies are glycoproteins comprising at least two heavy (H) chains and two light (L) chains inter-connected by disulfide bonds. Each heavy chain is comprised of a heavy chain variable region (abbreviated herein as $V_H$) and a heavy chain constant region. The heavy chain constant region is comprised of three domains, $C_{H1}$, $C_{H2}$ and $C_{H3}$. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (C1q) of the classical complement system. A "functional fragment" of a heavy chain constant region refers to a part of the constant region that retains the capability to mediate binding of the immunoglobulin to host tissues or factors, including various cells of the immune system (e.g., effector cells) and the first component (C1q) of the classical complement system, to initiate e.g., ADCC, CDC, ADCP and the like.

The term "antigen-binding portion" of an antibody (or simply "antibody portion"), as used herein, refers to one or more fragments of an antibody that retain the ability to specifically bind to an antigen (e.g., a CD70 protein). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_{H1}$ domains; (ii) a F(ab')$_2$ fragment, a bivalent fragment which may comprise two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment (Ward et al., (1989) *Nature* 341:544-546), which consists of a $V_H$ domain; (vi) an isolated complementarity determining region (CDR); and (viii) a nanobody, a heavy chain variable region containing a single variable domain and two constant domains. Furthermore, although the two domains of the Fv fragment, $V_L$ and $V_H$, are coded by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al., (1988) *Science* 242:423-426; and Huston et al., (1988) *Proc. Natl. Acad. Sci. USA* 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

An "isolated antibody", as used herein, is intended to refer to an antibody that is substantially free of other antibodies having different antigenic specificities (e.g., an isolated antibody that specifically binds a CD70 protein is substantially free of antibodies that specifically bind antigens other than CD70 proteins). An isolated antibody that specifically binds a human CD70 protein may, however, have cross-reactivity to other antigens, such as CD70 proteins from other species. Moreover, an isolated antibody can be substantially free of other cellular material and/or chemicals.

The terms "monoclonal antibody" or "monoclonal antibody composition" as used herein refer to a preparation of antibody molecules of single molecular composition. A monoclonal antibody composition displays a single binding specificity and affinity for a particular epitope.

The term "mouse antibody", as used herein, is intended to include antibodies having variable regions in which both the framework and CDR regions are derived from mouse germline immunoglobulin sequences. Furthermore, if the antibody contains a constant region, the constant region also is derived from mouse germline immunoglobulin sequences. The mouse antibodies of the disclosure can include amino acid residues not encoded by mouse germline immunoglobulin sequences (e.g., mutations introduced by random or site-specific mutagenesis in vitro or by somatic mutation in vivo). However, the term "mouse antibody", as used herein, is not intended to include antibodies in which CDR sequences derived from the germline of another mammalian species have been grafted onto mouse framework sequences.

The term "chimeric antibody" refers to an antibody made by combining genetic material from a nonhuman source with genetic material from a human being. Or more generally, a chimeric antibody is an antibody having genetic material from a certain species with genetic material from another species.

The term "humanized antibody", as used herein, refers to an antibody from non-human species whose protein sequences have been modified to increase similarity to antibody variants produced naturally in humans.

The heavy chain variable region CDRs and the light chain variable region CDRs in the antibody or antigen binding portion thereof of the disclosure have been defined by the IMGT numbering system. However, as is well known in the art, CDR regions can also be determined by other systems such as Chothia, Kabat, AbM, or Contact numbering system/method, based on heavy chain/light chain variable region sequences.

The term "antibody dependent cellular cytotoxicity", "antibody dependent cell-mediated cytotoxicity" or "ADCC" refers to a mechanism of cell-mediated immune defense whereby an effector cell of the immune system actively lyses a target cell bound by e.g., the anti-CD70 antibodies.

The term "antibody dependent cellular phagocytosis" or "ADCP" is a mechanism of immune defense where the interaction between the Fc domain of an antibody or an antigen binding portion thereof and activating FcRs on phagocytes (i.e., macrophages, granulocytes and dendritic cells) triggers engulfment of opsonized cells bound by the antibody or antigen binding portion thereof, eventually causing degradation of target cells.

The term "complement dependent cytotoxicity", "antibody dependent complement dependent cytotoxicity" or "CDC" refers to a mechanism of antibody mediated immunity where an antibody or an antigen binding portion thereof binds to the complement component C1q and activates the classical complement cascade, leading to the formation of a membrane attack complex (MAC) on the surface of target cells bound by the antibody or antigen binding portion thereof and subsequent target cell lysis.

The term "$EC_{50}$", also known as half maximal effective concentration, refers to the concentration of an antibody or an antigen binding portion thereof which induces a response halfway between the baseline and maximum after a specified exposure time.

The term "$IC_{50}$", also known as half maximal inhibitory concentration, refers to the concentration of an antibody or an antigen binding portion thereof which inhibits a specific biological or biochemical function by 50% relative to the absence of the antibody or antigen binding portion thereof.

The term "chimeric antigen receptor" or "CAR" refers to an engineered receptor that grafts a defined specificity onto an immune effector cell, typically a T cell, and augments T-cell function. The new generation CAR comprises a) an extracellular binding domain, b) a transmembrane domain, c) an intracellular signaling domain, and optionally a signal peptide on the N terminus of the extracellular binding domain. The CD27-CAR of the disclosure comprises a signal peptide, an extracellular domain of CD27, a CD8a hinge, a CD28 transmembrane domain, an intracellular domain, and a CD3 signaling domain.

The term "subject" includes any human or nonhuman animal. The term "nonhuman animal" includes all vertebrates, e.g., mammals and non-mammals, such as non-human primates, sheep, dogs, cats, cows, horses, chickens, amphibians, and reptiles, although mammals are preferred, such as non-human primates, sheep, dogs, cats, cows and horses.

As used herein, "sequence identity" refers to the percent of nucleotides/amino acid residues in a subject sequence that are identical to nucleotides/amino acid residues in a reference sequence, after aligning the sequences and, if necessary, introducing gaps, to achieve the maximum percent sequence identity between the sequences. Pairwise and multiple sequence alignment for the purposes of determining percent sequence identity between two or more amino acid or nucleic acid sequences can be achieved in various ways known to a person of skill in the art, for instance, using the publicly available computer software such as ClustalOmega, T-coffee, Kalign and MAFFT. When using such softwares, the default parameters, e.g. for gap penalty and extension penalty, are preferably used.

The term "therapeutically effective amount" means an amount of the antibody or antigen-binding portion thereof of the present disclosure sufficient to prevent or ameliorate the symptoms associated with a disease or condition (such as an inflammatory disease) and/or lessen the severity of the disease or condition. A therapeutically effective amount is understood to be in context to the condition being treated, where the actual effective amount is readily discerned by those of skill in the art.

In an embodiment, an antibody of the disclosure comprises a heavy and/or light chain variable region sequences of CDR1, CDR2 and CDR3 sequences which differ from those of the anti-CD70 antibodies of the present disclosure by one or more conservative modifications. It is understood in the art that certain conservative sequence modification can be made which do not remove antigen binding.

As used herein, the term "conservative sequence modifications" is intended to refer to amino acid modifications that do not significantly affect or alter the binding characteristics of the antibody or antigen binding portion thereof containing the amino acid sequence. Such conservative modifications include amino acid substitutions, additions and deletions. Modifications can be introduced into an antibody or an antigen binding portion thereof of the disclosure by standard techniques known in the art, such as site-directed mutagenesis and PCR-mediated mutagenesis. Conservative amino acid substitutions are ones in which the amino acid residue is replaced with an amino acid residue having a similar side chain Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody or an antigen binding portion thereof of the disclosure can be replaced with other amino acid residues from the same side chain family and the altered antibody can be tested for retained function (i.e., the functions set forth above) using the functional assays described herein.

Antibodies of the disclosure can be prepared using an antibody having one or more of the $V_H/V_L$ sequences of the anti-CD70 antibody of the present disclosure as starting material to engineer a modified antibody. An antibody can be engineered by modifying one or more residues within one or both variable regions (i.e., $V_H$ and/or $V_L$), for example within one or more CDR regions and/or within one or more framework regions. Additionally or alternatively, an antibody or an antigen binding portion thereof can be engineered by modifying residues within the constant region(s), for example to alter the effector function(s) of the antibody.

In certain embodiments, CDR grafting can be used to engineer variable regions of antibodies. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties.

Accordingly, another embodiment of the disclosure pertains to an isolated monoclonal antibody, or antigen binding portion thereof, comprising a heavy chain variable region comprising CDR1, CDR2, and CDR3 sequences comprising the sequences of the present disclosure, as described above, and/or a light chain variable region comprising CDR1, CDR2, and CDR3 sequences comprising the sequences of the present disclosure, as described above. While these antibodies contain the $V_H$ and $V_L$ CDR sequences of the monoclonal antibody of the present disclosure, they can contain different framework sequences. Such framework sequences can be obtained from public DNA databases or published references that include germline antibody gene sequences. For example, germline DNA sequences for human heavy and light chain variable region genes can be found in the "VBase" human germline sequence database (available on the Internet at www.mrc-cpe.cam.ac.uk/vbase). As another example, the germline DNA sequences for human heavy and light chain variable region genes can be found in the Genbank database. Preferred framework sequences for use in the antibodies of the disclosure are those that are structurally similar to the framework sequences used by antibodies of the disclosure. The $V_H$ CDR1, CDR2, and CDR3 sequences can be grafted onto framework regions that have the identical sequence as that found in the germline immunoglobulin gene from which the framework sequence derives, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody.

Another type of variable region modification is to mutate amino acid residues within the $V_H$ and/or $V_L$ CDR1, CDR2 and/or CDR3 regions to thereby improve one or more binding properties (e.g., affinity) of the antibody of interest. Site-directed mutagenesis or PCR-mediated mutagenesis can be performed to introduce the mutation(s) and the effect on antibody binding, or other functional property of interest, can be evaluated in in vitro or in vivo assays as known in the art. Preferably conservative modifications (as known in the art) are introduced. The mutations can be amino acid substitutions, additions or deletions, but are preferably substitutions. Moreover, typically no more than one, two, three, four or five residues within a CDR region are altered.

Engineered antibodies of the disclosure include those in which modifications have been made to framework residues within $V_H$ and/or $V_L$, e.g. to improve the properties of the antibody. Typically, such framework modifications are made to decrease the immunogenicity of the antibody. For example, one approach is to "back-mutate" one or more framework residues to the corresponding germline sequence. More specifically, an antibody that has undergone somatic mutation can contain framework residues that differ from the germline sequence from which the antibody is derived. Such residues can be identified by comparing the antibody framework sequences to the germline sequences from which the antibody is derived.

Another type of framework modification involves mutating one or more residues within the framework region, or even within one or more CDR regions, to remove T cell epitopes to thereby reduce the potential immunogenicity of the antibody.

In addition, or as an alternative to modifications made within the framework or CDR regions, antibodies of the disclosure can be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the disclosure can be chemically modified (e.g., one or more chemical moieties can be attached to the antibody) or be modified to alter its glycosylation, again to alter one or more functional properties of the antibody.

In one embodiment, the hinge region between the $C_{H1}$ and $C_{H2}$ regions is modified in such that the number of cysteine residues in the hinge region is altered, e.g., increased or decreased. The number of cysteine residues in the hinge region is altered to, for example, facilitate assembly of the light and heavy chains or to increase or decrease the stability of the antibody.

In another embodiment, the Fc hinge region of an antibody is mutated to increase or decrease the biological half-life of the antibody. More specifically, one or more amino acid mutations are introduced into the $C_{H2}$-$C_{H3}$ domain interface region of the Fc-hinge fragment such that the antibody has impaired Staphylococcyl protein A (SpA) binding relative to native Fc-hinge domain SpA binding.

In still another embodiment, the glycosylation of an antibody is modified. For example, a glycosylated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such a glycosylation may increase the affinity of the antibody for antigen. Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the disclosure to thereby produce an antibody with altered glycosylation.

Monoclonal antibodies (mAbs) of the present disclosure can be produced using the well-known somatic cell hybridization (hybridoma) technique of Kohler and Milstein (1975) *Nature* 256: 495. Other embodiments for producing monoclonal antibodies include viral or oncogenic transformation of B lymphocytes and phage display techniques. Chimeric or humanized antibodies are also well known in the art.

Antibodies of the disclosure also can be produced in a host cell transfectoma using, for example, a combination of recombinant DNA techniques and gene transfection methods as is well known in the art (e.g., Morrison, S. (1985) Science 229:1202). In one embodiment, DNA encoding partial or full-length light and heavy chains obtained by standard molecular biology techniques is inserted into one or more expression vectors such that the genes are operatively linked to transcriptional and translational regulatory sequences. In this context, the term "operatively linked" is intended to mean that an antibody gene is ligated into a vector such that transcriptional and translational control sequences within the vector serve their intended function of regulating the transcription and translation of the antibody gene.

The term "regulatory sequence" is intended to include promoters, enhancers and other expression control elements (e.g., polyadenylation signals) that control the transcription or translation of the antibody genes. Such regulatory sequences are described, e.g., in Goeddel (Gene Expression Technology. Methods in Enzymology 185, Academic Press, San Diego, Calif. (1990)). Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, e.g., the adenovirus major late promoter (AdMLP) and polyoma. Alternatively, non-viral regulatory sequences can be used, such as the ubiquitin promoter or β-globin promoter. Still further, regulatory elements composed of sequences from different sources, such as the SRα promoter system, which contains sequences from the SV40 early promoter and the long terminal repeat of human T cell leukemia virus type 1 (Takebe et al., (1988) Mol. Cell. Biol. 8:466-472). The expression vector and expression control sequences are chosen to be compatible with the expression host cell used.

The antibody light chain gene and the antibody heavy chain gene can be inserted into the same or separate expression vectors. In preferred embodiments, the variable regions are used to create full-length antibody genes of any antibody isotype by inserting them into expression vectors already encoding heavy chain constant and light chain constant regions of the desired isotype such that the $V_H$ segment is operatively linked to the $C_H$ segment(s) within the vector and the $V_L$ segment is operatively linked to the $C_L$ segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes and regulatory sequences, the recombinant expression vectors of the disclosure can carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216; 4,634,665 and 5,179,017).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the disclosure in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody.

Preferred mammalian host cells for expressing the recombinant antibodies of the disclosure include Chinese Hamster Ovary (CHO cells), NSO myeloma cells, COS cells and SP2 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Antibodies of the disclosure can be conjugated to a therapeutic agent to form an immunoconjugate such as an antibody-drug conjugate (ADC). Suitable therapeutic agents include cytotoxins, alkylating agents, DNA minor groove binders, DNA intercalators, DNA crosslinkers, histone deacetylase inhibitors, nuclear export inhibitors, proteasome inhibitors, topoisomerase I or II inhibitors, heat shock protein inhibitors, tyrosine kinase inhibitors, antibiotics, and anti-mitotic agents. In the ADC, the antibody and therapeutic agent preferably are conjugated via a linker cleavable such as a peptidyl, disulfide, or hydrazone linker. More preferably, the linker is a peptidyl linker such as Val-Cit, Ala-Val, Val-Ala-Val, Lys-Lys, Pro-Val-Gly-Val-Val, Ala-Asn-Val, Val-Leu-Lys, Ala-Ala-Asn, Cit-Cit, Val-Lys, Lys, Cit, Ser, or Glu.

In another aspect, the present disclosure features bispecific molecules comprising one or more antibodies of the disclosure linked to at least one other functional molecule, e.g., another peptide or protein (e.g., another antibody or ligand for a receptor) to generate a bispecific molecule that binds to at least two different binding sites or target molecules. Thus, as used herein, "bispecific molecule" includes molecules that have three or more specificities. In an embodiment, a bispecific molecule has, in addition to an anti-Fc binding specificity and an anti-CD70 binding specificity, a third specificity. The third specificity can be for CD47, to more accurately target tumor cells while releasing other $CD70^+$ cells such as $CD70^+$ immune cells.

Bispecific molecules may be in many different formats and sizes. At one end of the size spectrum, a bispecific molecule retains the traditional antibody format, except that, instead of having two binding arms of identical specificity, it has two binding arms each having a different specificity. At the other extreme are bispecific molecules consisting of two single-chain antibody fragments (scFv's) linked by a peptide chain, a so-called $Bs(scFv)_2$ construct. Intermediate-sized bispecific molecules include two different F(ab) fragments linked by a peptidyl linker. Bispecific molecules of these and other formats can be prepared by genetic engineering, somatic hybridization, or chemical methods.

Also provided herein are a chimeric antigen receptor (CAR) containing an anti-CD70 scFv, the anti-CD70 scFv comprising CDRs and heavy/light chain variable regions described herein.

The anti-CD70 CAR may comprise (a) an extracellular antigen binding domain comprising an anti-CD70 scFv; (b) a transmembrane domain; and (c) an intracellular signaling domain.

In another aspect, the disclosure provides nucleic acid molecules that encode heavy and/or light chain variable regions, or CDRs, of the antibodies of the disclosure. The nucleic acids can be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques. A nucleic acid of the disclosure can be, e.g., DNA or RNA and may or may not contain intronic sequences. In a preferred embodiment, the nucleic acid is a cDNA molecule.

Nucleic acids of the disclosure can be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g., using phage display techniques), a nucleic acid encoding such antibodies can be recovered from the gene library.

Preferred nucleic acids molecules of the disclosure include those encoding the $V_H$ and $V_L$ sequences of the anti-CD70 monoclonal antibody or the CDRs. Once DNA fragments encoding $V_H$ and $V_L$ segments are obtained, these DNA fragments can be further manipulated by standard recombinant DNA techniques, for example to convert the variable region genes to full-length antibody chain genes, to Fab fragment genes or to a scFv gene. In these manipulations, a $V_L$- or $V_H$-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the $V_H$ region can be converted to a full-length heavy chain gene by operatively linking the $V_H$-encoding DNA to another DNA molecule encoding heavy chain constant regions ($C_{H1}$, $C_{H2}$ and $C_{H3}$). The sequences of human heavy chain constant region genes are known in the art and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1 or IgG2 constant region. For a Fab fragment heavy chain gene, the $V_H$-encoding DNA can be operatively linked to another DNA molecule encoding only the heavy chain $C_{H1}$ constant region.

The isolated DNA encoding the $V_L$ region can be converted to a full-length light chain gene (as well as a Fab light chain gene) by operatively linking the $V_L$-encoding DNA to another DNA molecule encoding the light chain constant region, $C_L$. The sequences of human light chain constant region genes are known in the art and DNA fragments encompassing these regions can be obtained by standard PCR amplification. In preferred embodiments, the light chain constant region can be a kappa or lambda constant region.

To create a scFv gene, the $V_H$- and $V_L$-encoding DNA fragments are operatively linked to another fragment encoding a flexible linker, such that the $V_H$ and $V_L$ sequences can be expressed as a contiguous single-chain protein, with the $V_L$ and $V_H$ regions joined by the flexible linker.

In another aspect, the present disclosure provides a pharmaceutical composition which may comprise one or more antibodies or antigen-binding portions thereof, the immunoconjugates, bispecifics, CAR-expressing immune cells, nucleic acid molecules, expression vectors, or host cells of the present disclosure formulated together with a pharmaceutically acceptable carrier. The composition may optionally contain one or more additional pharmaceutically active ingredients, such as an anti-tumor agent, such as IMM01, a SIRPalphaD1-Fc fusion protein.

The pharmaceutical composition can comprise any number of excipients. Excipients that can be used include carriers, surface active agents, thickening or emulsifying agents, solid binders, dispersion or suspension aids, solubilizers, colorants, flavoring agents, coatings, disintegrating agents, lubricants, sweeteners, preservatives, isotonic agents, and combinations thereof.

The pharmaceutical composition may be suitable for intravenous, intramuscular, subcutaneous, parenteral, spinal or epidermal administration (e.g., by injection or infusion). Depending on the route of administration, the active ingredient can be coated in a material to protect it from the action of acids and other natural conditions that may inactivate it. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, the pharmaceutical composition of the disclosure can be administered via a non-parenteral route, such as a topical, epidermal or mucosal route of administration, e.g., intranasally, orally, vaginally, rectally, sublingually or topically.

Pharmaceutical compositions can be in the form of sterile aqueous solutions or dispersions. They can also be formulated in a microemulsion, liposome, or other ordered structure suitable to high drug concentration.

The amount of active ingredient which can be combined with a carrier material to produce a single dosage form will vary depending upon the subject being treated and the particular mode of administration and will generally be that amount of the composition which produces a therapeutic effect. Generally, out of one hundred percent, this amount will range from about 0.01% to about 99% of active ingredient in combination with a pharmaceutically acceptable carrier.

Dosage regimens are adjusted to provide the optimum desired response (e.g., a therapeutic response). For example, a single bolus can be administered, several divided doses can be administered over time or the dose can be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active ingredient calculated to produce the desired therapeutic effect in association with the required pharmaceutical carrier. Alternatively, antibody can be administered as a sustained release formulation, in which case less frequent administration is required.

For administration of the antibody, the dosage may range from about 0.0001 to 100 mg/kg.

The pharmaceutical composition can be a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. See, e.g., Sustained and Controlled Release Drug Delivery Systems, J. R. Robinson, ed., Marcel Dekker, Inc., New York, 1978.

Therapeutic compositions can be administered via medical devices such as (1) needleless hypodermic injection devices (e.g., U.S. Pat. Nos. 5,399,163; 5,383,851; 5,312,335; 5,064,413; 4,941,880; 4,790,824; and 4,596,556); (2) micro-infusion pumps (U.S. Pat. No. 4,487,603); (3) transdermal devices (U.S. Pat. No. 4,486,194); (4) infusion apparatuses (U.S. Pat. Nos. 4,447,233 and 4,447,224); and (5) osmotic devices (U.S. Pat. Nos. 4,439,196 and 4,475,196); the disclosures of which are incorporated herein by reference.

In certain embodiments, the monoclonal antibodies of the disclosure can be formulated to ensure proper distribution in vivo. For example, to ensure that the therapeutic antibody of the disclosure cross the blood-brain barrier, they can be formulated in liposomes, which may additionally comprise targeting moieties to enhance selective transport to specific cells or organs.

The pharmaceutical composition of the disclosure may have multiple in vitro and in vivo uses. For example, the pharmaceutical composition can be used to treat tumors, or more generally speaking, to enhance immune responses in tumor patients. The pharmaceutical composition may be administered to human subjects, to e.g., inhibit tumor growth.

Given the ability of the pharmaceutical composition to inhibit tumor cell proliferation and survival, the present application provides a method of inhibiting growth of tumor cells in a subject in need thereof, comprising administering to the subject the pharmaceutical composition of the disclosure, such that the tumor growth is inhibited in the subject. The tumor that may be treated by the pharmaceutical composition of the disclosure includes the solid tumor and the blood tumor, including, but not limited to, kidney cancer, myelodysplastic syndromes, cutaneous T-cell lymphomas, nasopharyngeal carcinoma, Epstein-Barr virus induced cancer, Hodgkin lymphoma (HL), non-Hodgkin lymphoma (NHL), diffuse large B cell lymphoma, follicular lymphoma, B lymphocytic leukemia, Burkitt lymphoma, multiple myeloma, Waldenstrom macroglobulinemia, thymic carcinoma, glioblastoma, brain cancer, osteosarcoma, melanoma, ovarian cancer, renal cell carcinoma, breast cancer, squamous cell carcinoma of the head and neck, colorectal cancer, mantle cell lymphoma, prostate adenocarcinoma, colorectal adenocarcinoma, lymphoma of the central nervous system, and non-small cell lung cancer, original or metastatic.

Further, given the correlation between CD70 and inflammatory diseases, the present application provides a method for treating or ameliorating an inflammatory disease in a subject in need thereof, comprising administering to the subject the pharmaceutical composition of the disclosure. The inflammatory disease may be an autoimmune disease, including, but not limited to, arthritis, inflammatory bowel disease, and lupus.

The pharmaceutical composition of the disclosure may be administered with one or more additional agents that may effectively inhibit tumor growth or reduce/eliminate inflammation in a subject. In certain embodiments, the present application provides a method for inhibiting tumor growth in a subject in need thereof, comprising administering to the subject the pharmaceutical composition of the disclosure and IMM01, a SIRPalphaD1-Fc fusion protein.

The combination of therapeutic agents discussed herein can be administered concurrently as a single composition in a pharmaceutically acceptable carrier, or concurrently as separate compositions with each agent in a pharmaceutically acceptable carrier. In another embodiment, the combination of therapeutic agents can be administered sequentially.

Furthermore, if more than one dose of the combination therapy is administered sequentially, the order of the sequential administration can be reversed or kept in the same order at each time point of administration, sequential administrations can be combined with concurrent administrations, or any combination thereof.

The present application is now further described with the non-limiting examples below.

EXAMPLES

The structures of the exemplary anti-CD70 antibodies of the disclosure, IMM40C, IMM40H and IMM40M, are shown in FIG. 1 and described below in further details.

IMM40C is an IgG antibody, comprising a mouse heavy chain variable region, a human IgG1 constant region, a mouse light chain variable region, and a human kappa constant region, respectively having the amino acid sequences of SEQ ID NOs: 7, 11, 8 and 12.

IMM40H is an IgG antibody, comprising a humanized heavy chain variable region, a human IgG1 constant region, a humanized light chain variable region, and a human kappa constant region, respectively having the amino acid sequences of SEQ ID NOs: 9, 11, 10 (X=N) and 12.

IMM40M is an IgG antibody, comprising a humanized heavy chain variable region, a human IgG1 constant region, a humanized light chain variable region, and a human kappa constant region, respectively having the amino acid sequences of SEQ ID NOs: 9, 11, 10 (X=E) and 12. Compared to IMM40H, IMM40M comprises a N85E mutation in the light chain variable region, which removes a glycosylation site represented by *.

IMM01 is a SIRPαD1-Fc fusion protein that binds CD47, as disclosed in US2021/0024598A1, comprising two SIRPαD1 mutants linked to two Fc fragments, wherein each monomer of the formed dimer has the amino acid sequence of SEQ ID NO: 17. The SIRPαD1 mutant in IMM01 contains a N80A mutation in SEQ ID NO: 17 which removes a glycosylation site.

Cusatuzumab is an anti-CD70 IgG antibody, comprising a heavy chain and a light chain respectively having the amino acid sequences of SEQ ID NOs: 20 and 21.

Example 1. Generation and Humanization of Anti-CD70 Antibodies, and Vector Construction for Antibody Expression Mice were immunized with human CD70 proteins, and those with good titers were selected for antibody preparation. Briefly, spleen cells from the selected mice were fused with myeloma cells, and hybridoma colonies that secreted anti-CD70 antibodies having high CD70 binding capabilities were picked out and subcloned by limited dilution. Monoclonal antibodies were generated and sequenced. One antibody, as referred to as IMM40C, had a heavy chain variable region and a light chain variable region with amino acid sequences set forth in SEQ ID NOs: 7 and 8, respectively.

IMM40C was later humanized using the well-established CDR-grafting method. One exemplary humanized antibody IMM40H was obtained with a heavy chain variable region and a light chain variable region respectively having the amino acid sequences set forth in SEQ ID NOs: 9 and 10 (X=N). IMM40H was further modified at the light chain variable region with a N85E mutation to provide IMM40M, wherein the N85E mutation can remove the glycosylation site. IMM40M's heavy and light chain variable regions contained the amino acid sequences set forth in SEQ ID NOs: 9 and 10 (X=E), respectively.

The full length coding sequences of the exemplary antibodies were designed artificially.

Specifically, for IMM40C's heavy chain, 57 nucleotides encoding the signal peptide of mouse IgG1 heavy chain (SEQ ID NO: 18) were added to the 5' end of the coding sequence of IMM40C's heavy chain variable region plus constant region (SEQ ID NO: 13), and a Kozak sequence (SEQ ID NO: 19) was added to the 5' end of the signal peptide sequence. Lastly, HindIII and NheI restriction sites were added to the 5' and 3' ends of the resulting sequence, respectively. For IMM40C's light chain, the same signal sequence as well as the Kozak sequence was added to the 5' end of the coding sequence for IMM40C's light chain variable region plus constant region (SEQ ID NO: 14), and HindIII and XbaI restriction sites were added to the 5' and 3' ends of the resulting sequence, respectively. The sequences were synthesized by GenScript and cloned into pMac-H and pMac-L vectors, respectively.

For IMM40H's heavy chain, 57 nucleotides encoding the signal peptide of mouse IgG1 heavy chain (SEQ ID NO: 18) were added to the 5' end of the coding sequence of IMM40H's heavy chain variable region plus constant region (SEQ ID NO: 15), and a Kozak sequence (SEQ ID NO: 19) was added to the 5' end of the signal peptide sequence. Lastly, HindIII and NheI restriction sites were added to the 5' and 3' ends of the resulting sequence, respectively. For IMM40H's light chain, the same signal sequence as well as the Kozak sequence was added to the 5' end of the coding sequence for IMM40H's light chain variable region plus constant region (SEQ ID NO: 16, N1=A, N2=C), and HindIII and XbaI restriction sites were added to the 5' and 3' ends of the resulting sequence, respectively. The sequences were synthesized by GenScript and cloned into pMac-H and pMac-L vectors, respectively.

For IMM40M's heavy chain, 57 nucleotides encoding the signal peptide of mouse IgG1 heavy chain (SEQ ID NO: 18) were added to the 5' end of the coding sequence of IMM40M's heavy chain variable region plus constant region (SEQ ID NO: 15), and a Kozak sequence (SEQ ID NO: 19) was added to the 5' end of the signal peptide sequence. Lastly, HindIII and NheI restriction sites were added to the 5' and 3' ends of the resulting sequence, respectively. For IMM40M's light chain, the same signal sequence as well as the Kozak sequence was added to the 5' end of the coding sequence for IMM40M's light chain variable region plus constant region (SEQ ID NO: 16, N1=G, N2=A), and HindIII and XbaI restriction sites were added to the 5' and 3' ends of the resulting sequence, respectively. The sequences were synthesized by GenScript and cloned into pMac-H and pMac-L vectors, respectively.

These antibodies of the disclosure were expressed using CHO-S cells with the vectors constructed above. Briefly, CHO-S cells were seeded at a density of $1 \times 10^6$ cells/ml in TransFx-CTMCHO Transient transfection Medium (Hyclone) containing 6 mM glutamine one day before transient transfection. The heavy chain and light chain expression vectors, at a mass ratio of 1:1 with a total DNA amount of 1 µg/ml, were added to OPTI-MEM medium (Gibco) whose volume was 1/20 of that of the TransFx-CTMCHO Transient transfection Medium as used. PEI (polyethylenimine, MW 40,000, Cat #24765-1, polysciences) at 1 mg/ml was added to OPTI-MEM medium (Gibco) whose volume was 1/20 of that of the TransFx-CTMCHO Transient transfection Medium as used. The PEI dilution was slowly added to, mixed and incubated at room temperature for 20 min with the diluted DNAs, at a PEI:DNA mass ratio of 4:1. Then, the DNA/PEI mixture was added to the cell cultures, and the cells were incubated in a 37° C. and 5% $CO_2$ cell culture incubator with shaking at 110 rpm. Transfection enhancer (1 mM sodium butyrate, 0.25% V/V DMSO) was added two days later, and the temperature was decreased to 33° C. When the cell viability dropped to ~50%, the cell culture supernatant was harvested by centrifugation at 3000 rpm for 5 min, and subjected to protein purification using Protein A chromatography.

Example 2. Exemplary Antibody Bound to Cell Surface CD70s

Cells, i.e., Chinese hamster ovary cells expressing human CD70s, $CD47^+CD70^+$ U266 cells, and $CD47^+CD70^+$ Raji cells, in 100 µl culture medium (PBS with 1% BSA, also referred to as 1% BSA-PBS) at a cell density of $1 \times 10^6$/ml were incubated with 100 µl serially diluted IMM40C, IMM40H and IMM40M in 1% BSA-PBS, respectively, at 4° C. for 45 min. Cells were washed with 1% BSA-PBS once, and then incubated with 100 µl 1:500 diluted FITC-conjugated secondary antibody against human IgG-Fc (Cat #F9512, Sigma) at 4° C. for 45 min. Cells were washed once with 1% BSA-PBS, re-suspended in 200 µl 1% BSA-PBS, and then subject to FACS analysis using a flow cytometer (Merck Millipore, Guava® easyCyte 5HT).

Figure 2A:
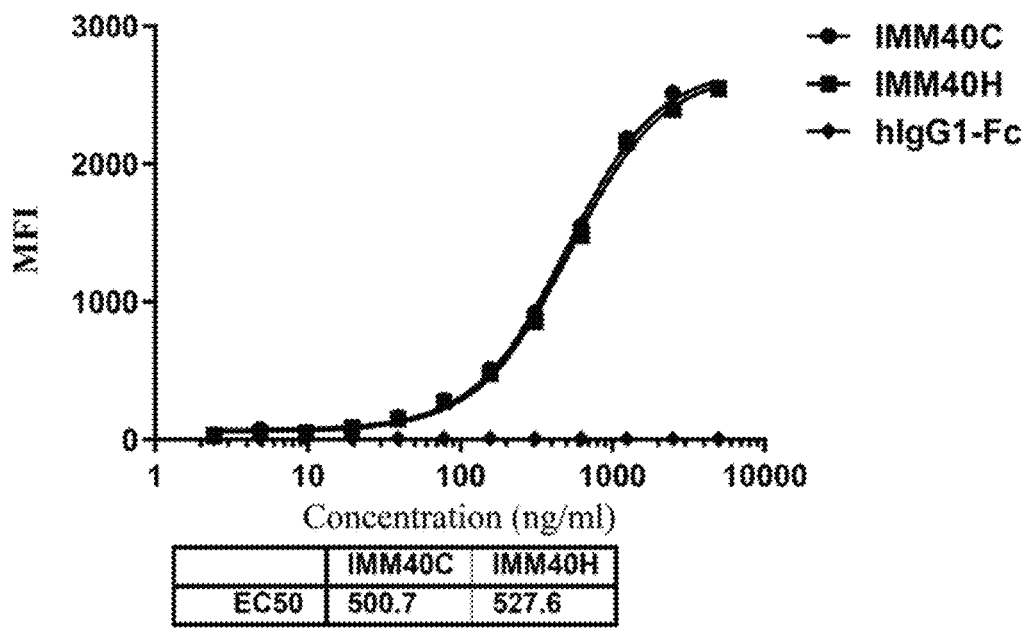
FIGS. 2A to 2F show the binding activities of IMM40C, IMM40H and IMM40M to human CD70-expressing Chinese hamster ovary (CHO) cells (A, E), CD47$^+$CD70$^+$ U266 cells (B, D, F), and CD47$^+$CD70$^+$ Raji cells (C), with cusatuzumab (an anti-CD70 antibody having heavy and light chain sequences set forth in SEQ ID NOs: 20 and 21), IMM01 (a SIRPalphaD1-Fc fusion protein, SEQ ID NO: 17), and/or hIgG1-Fc used as the controls.

As shown in FIG. 2A, IMM40C and IMM40H specifically bound $CD70^+$ CHO cells, without binding capability differences between the two, hIgG1-Fc was used as the negative control.

Figure 2B:
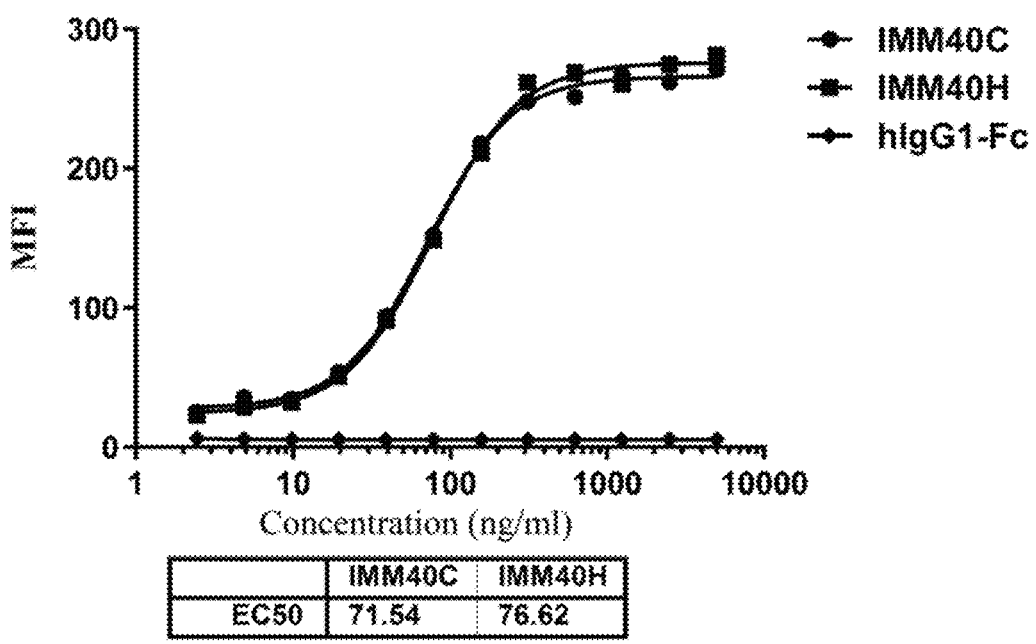

According to FIG. 2B, IMM40C and IMM40H specifically bound $CD70^+ CD47^+$ U266 cells, without binding capability differences between the two, hIgG1-Fc was used as the negative control.

Figure 2C:
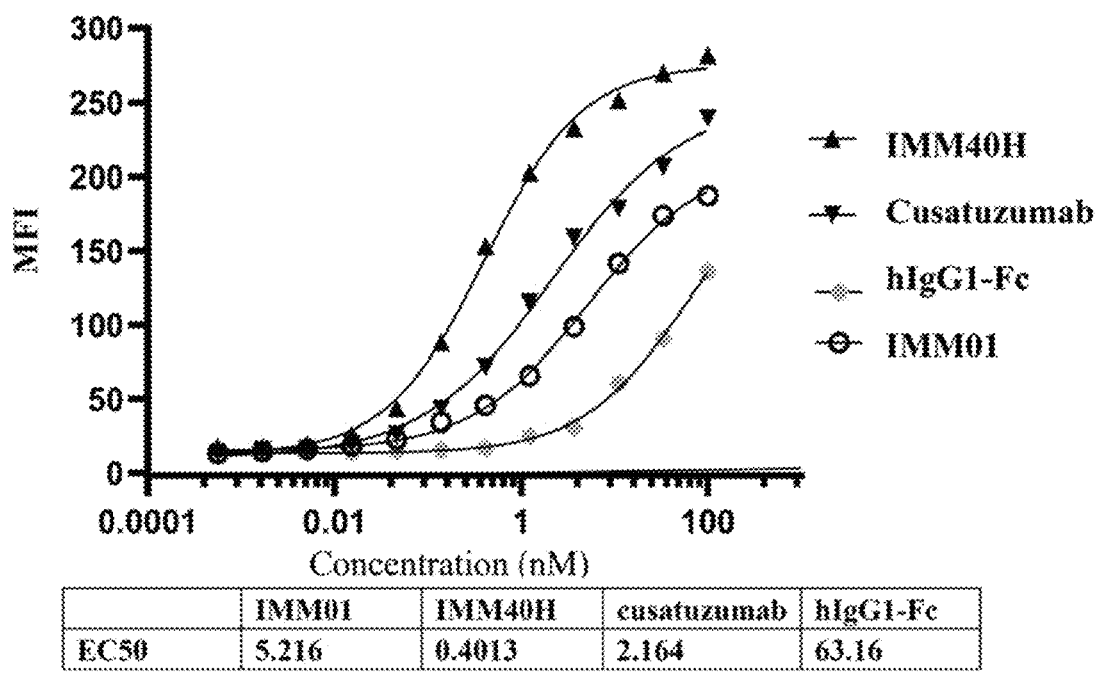

As shown in FIG. 2C, IMM40H specifically bound $CD70^+ CD47^+$ Raji cells, with a binding capability much higher than those of cusatuzumab and IMM01, hIgG1-Fc was used as the negative control.

Figure 2D:
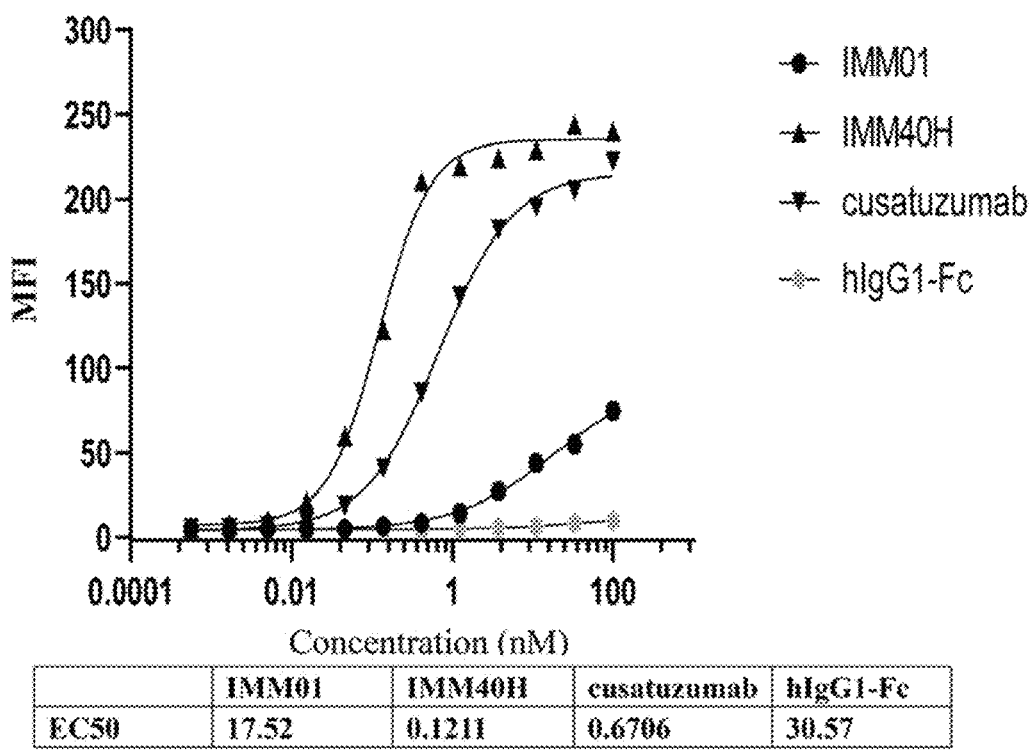

Similarly, as shown in FIG. 2D, IMM40H specifically bound $CD70^+CD47^+$ U266 cells, with a binding capability much higher than those of cusatuzumab and IMM01, hIgG1-Fc was used as the negative control.

Figure 2E:
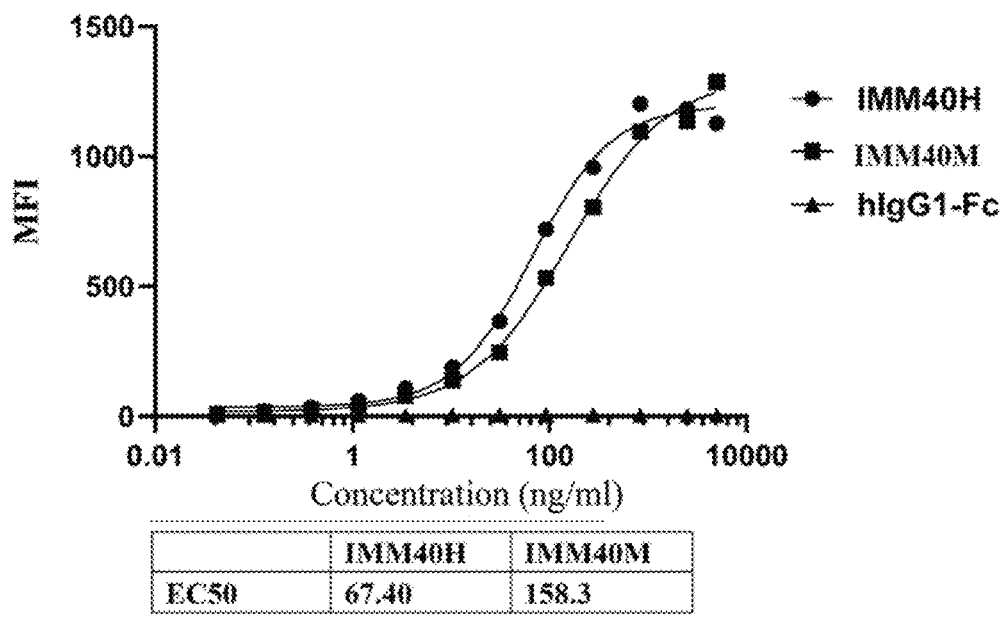

FIG. 2E showed the binding activities of IMM40H and IMM40M to $CD70^+$ CHO cells, with hIgG1-Fc used as the negative control. It can be seen these two antibodies bound to the cells with similar binding activities, with IMM40H' binding activity being a bit higher than that of IMM40M.

Figure 2F:
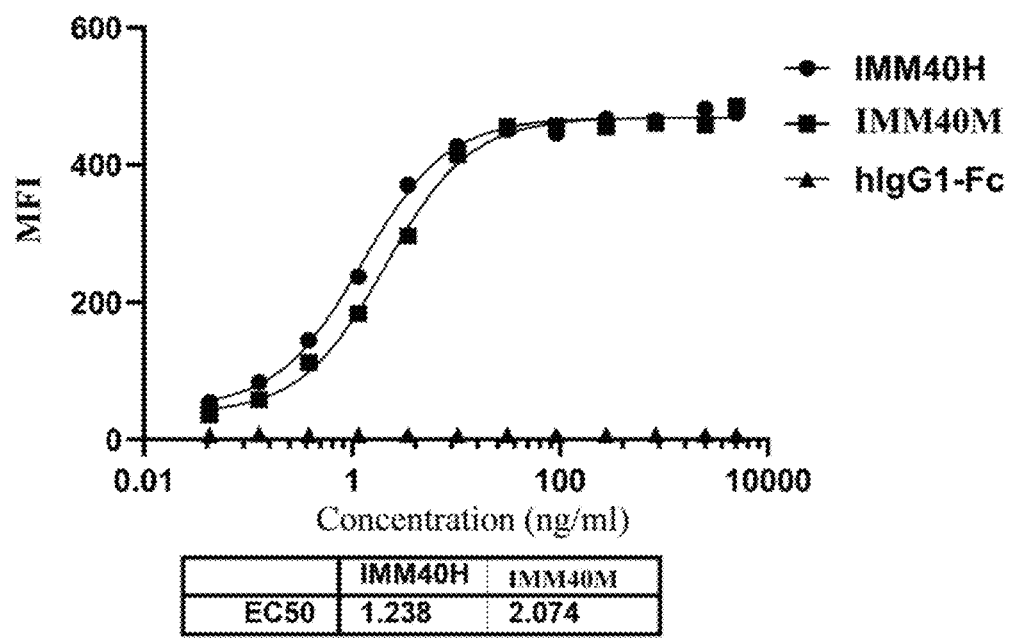

FIG. 2F showed the binding activities of IMM40H and IMM40M to $CD70^+ CD47^+$ U266 cells, with hIgG1-Fc used as the negative control. It can be seen these two antibodies bound to the cells with similar binding activities, with IMM40H' binding activity being a bit higher than that of IMM40M.

Example 3. Exemplary Antibody Inhibited CD27(ECD)-CD70 Binding/Interaction

Fifty µl of CHO cells expressing human CD70, at a density of $5 \times 10^5$/ml, were incubated with 50 µl serially diluted IMM40H, cusatuzumab and hIgG-Fc (3-fold dilution, starting at 900 nM), respectively. The resultant mixtures were added to a 96-well plate containing 50 µl 2.5 µg/ml biotin-CD27(ECD)-Fc (SEQ ID NO: 22, amino acid residues 1 to 172 coding for CD27 extracellular domain) in each well, and the plate was incubated at 4° C. for 45 min. The cells were washed with PBS and incubated with 100 µl PE-conjugated streptavidin (Cat #554061, Biolegend) for 45 min. Cells were washed twice, re-suspended in 200 µl PBS, and subject to FACS analysis.

Figure 3:
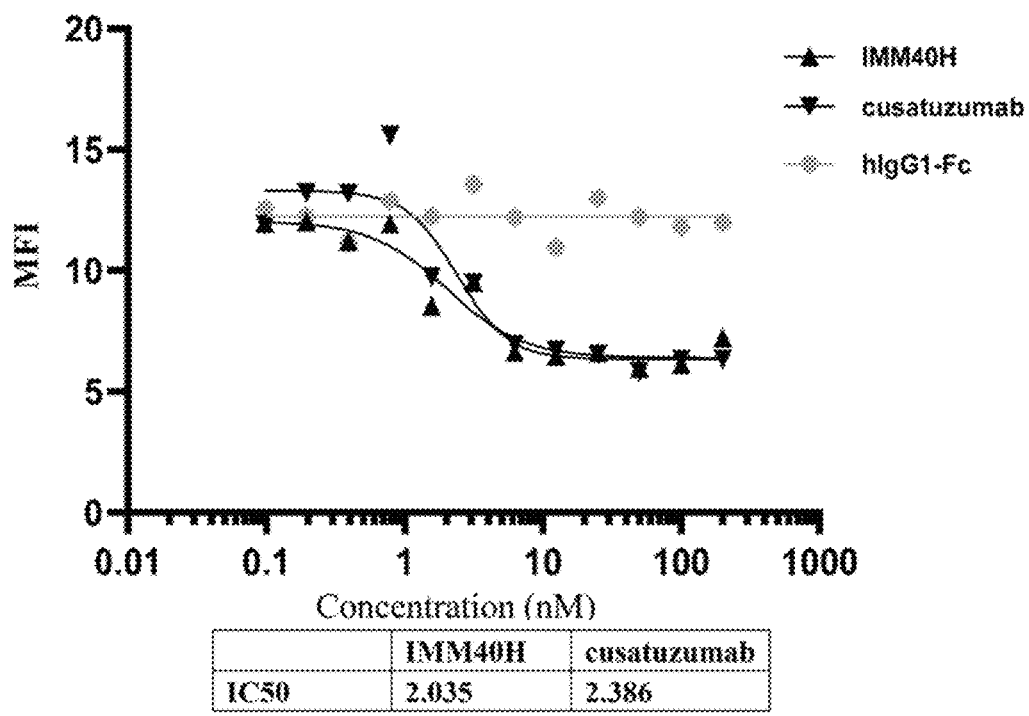
FIG. 3 shows the ability of IMM40H to block the binding of CD27(ECD)-Fc (SEQ ID NO: 22) to CD70$^+$ CHO cells, with cusatuzumab used as the positive control and hIgG1-Fc as the negative control.

As can be seen from FIG. 3, IMM40H blocked the binding of CD27(ECD)-Fc to $CD70^+ CD47^-$ CHO cells at an activity similar to that of cusatuzumab.

Example 4. Exemplary Antibody Inhibited CD27-CD70 Binding/Interaction

Fifty µl of $CD70^+$ Raji cells, at a density of $2 \times 10^5$/ml, were incubated with 50 µl serially diluted IMM40H, cusatuzumab, IMM01 and hIgG-Fc (4-fold dilution, starting at 16 ng/ml), respectively, at 37° C. for 45 min. The resultant mixtures were added with 50 µl $1 \times 10^6$/ml Jurkat cells expressing CD27-CARs (in house prepared, with the amino acid sequence of the CD27-CAR set forth in SEQ ID NO: 23, with amino acid residues 1 to 172 coding to CD27 extracellular domain), and incubated overnight at 37° C. The mixtures were added with 0.5% BSA-PBS and subject to centrifugation. The cells were re-suspended in 50 µl PE-conjugated antibody against human CD69 (1:100 diluted, Cat #sc-373799, Santa Cruz), incubated at 4° C. for 45 min, washed once with 0.5% BSA-PBS, re-suspended in 0.5% BSA-PBS, and subject to FACS analysis using a flow cytometer (Guava® easyCyte 5HT, Merck Millipore). The CD69 expression levels may indirectly reflect the binding of CD70s on Raji cells to CD27-CARs expressed by Jurkat cells.

Figure 4:
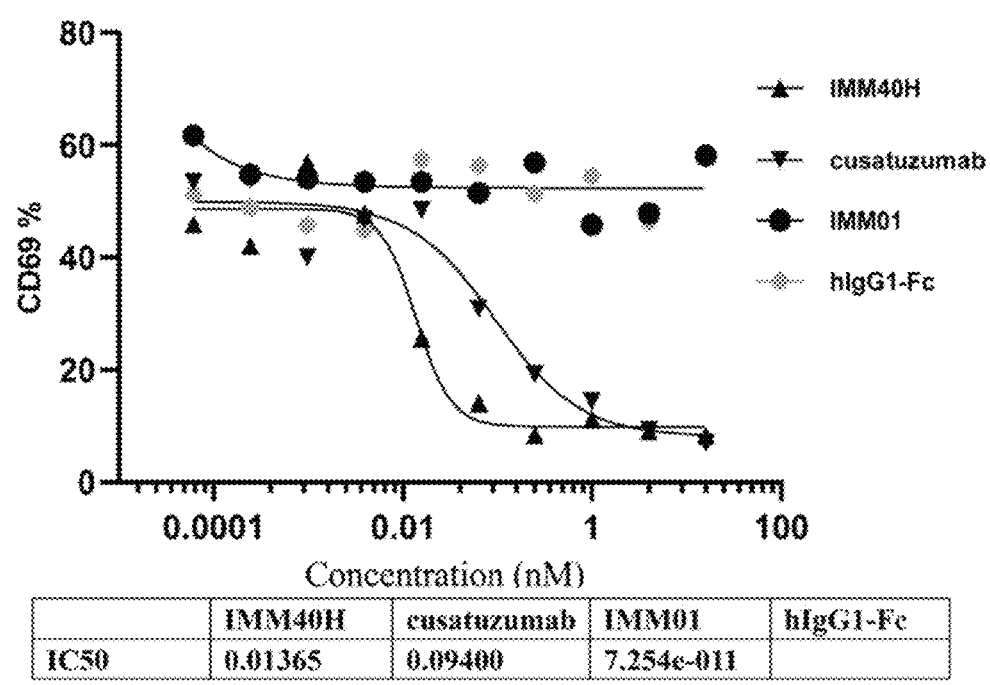
FIG. 4 shows the ability of IMM40H to block the binding of CD70$^+$ Raji cells to Jurkat cells expressing CD27-CAR (SEQ ID NO: 23), as measured by CD70-CD27 interaction induced CD69 expression levels, with cusatuzumab used as the positive control, IMM01 and hIgG1-Fc as the negative control.

As shown in FIG. 4, IMM40H blocked the binding of CD27-CARs to cell surface CD70s, with higher activity than that of cusatuzumab.

Example 5. Exemplary Antibody Induced High Antibody-Dependent Cell-Mediated Cytotoxicity (ADCC) Against CD70+ Cells CFSE (Cat #21888-25 mg, Sigma) at 1 mM was 1:500 diluted and used to label CD70+ tumor cells.

The CFSE-labeled tumor cells, as the target cells, in 50 µl culture medium at a density of 6×10$^5$/ml, were mixed at a 2:1 effector:target ratio with 100 µl 6×10$^5$/ml NK92MI cells stably expressing FcγRIIIa, as the effector cells. The mixed cells were cultured for 4 hours at 37° C. under 5% $CO_2$ with 50 µl serially diluted IMM40H, IMM01, IMM40H+IMM01 mixture, and hIgG-Fc (4-fold dilution, starting at 1 nM, for the IMM40H+IMM01 mixture, IMM40H and IMM01 both had the starting concentration at 1 nM), respectively. Then cell cultures were added with propidium iodide (PI) (Cat #P4170, Sigma) at a concentration of 5 µg/ml, and then subjected to FACS analysis for PI signals. Percent ADCC was calculated based on the following formula.

% Lysis=(% PI Positive Target Cells treated with IMM40H, IMM01 or IMM40+IMM01−% PI Positive Target Cells treated with negative control)/(100−% PI Positive Target Cells treated with negative control)*100

Figure 5A:
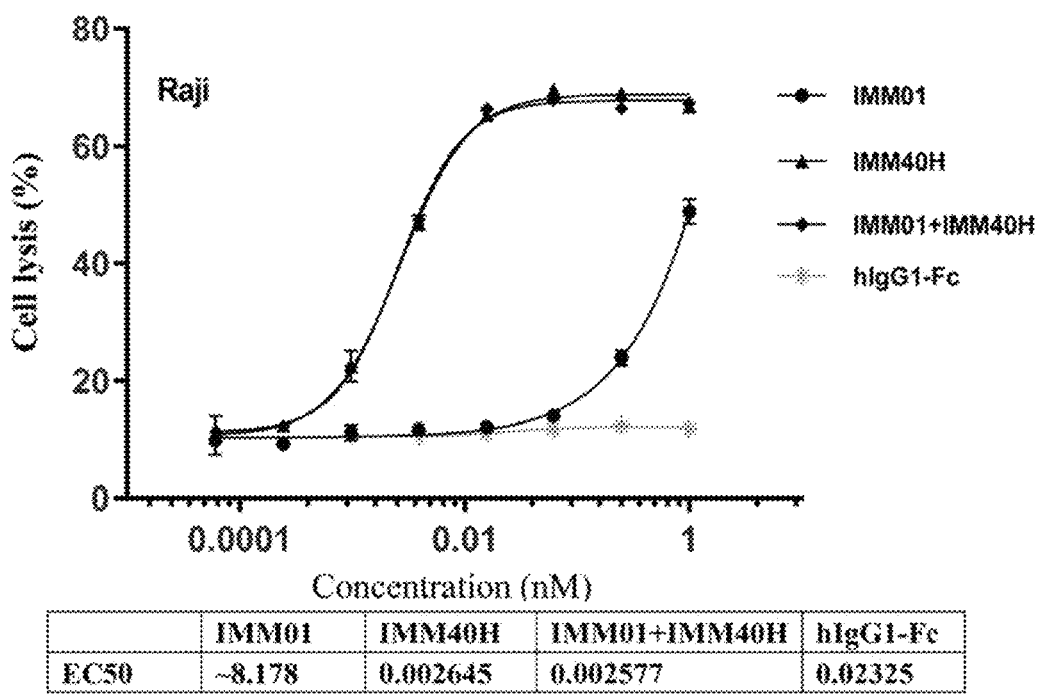
FIGS. 5A to 5D show the abilities of IMM40H and IMM40H+IMM01 to induce antibody dependent cell mediated cytotoxicity (ADCC) against CD47$^+$CD70$^+$ Raji cells (A), CD47$^+$CD70$^+$ U266 cells (B), CD47$^+$CD70$^+$ Daudi cells (C) and CD47$^+$CD70$^+$ Jeko-1 cells (D), with IMM01 and hIgG1-Fc used as the controls.

According to FIG. 5A, the ADCC against CD47+CD70+ Raji cells induced by IMM40H was similar to that induced by the IMM40H+IMM01 mixture, but much higher than that induced by IMM01.

Figure 5B:
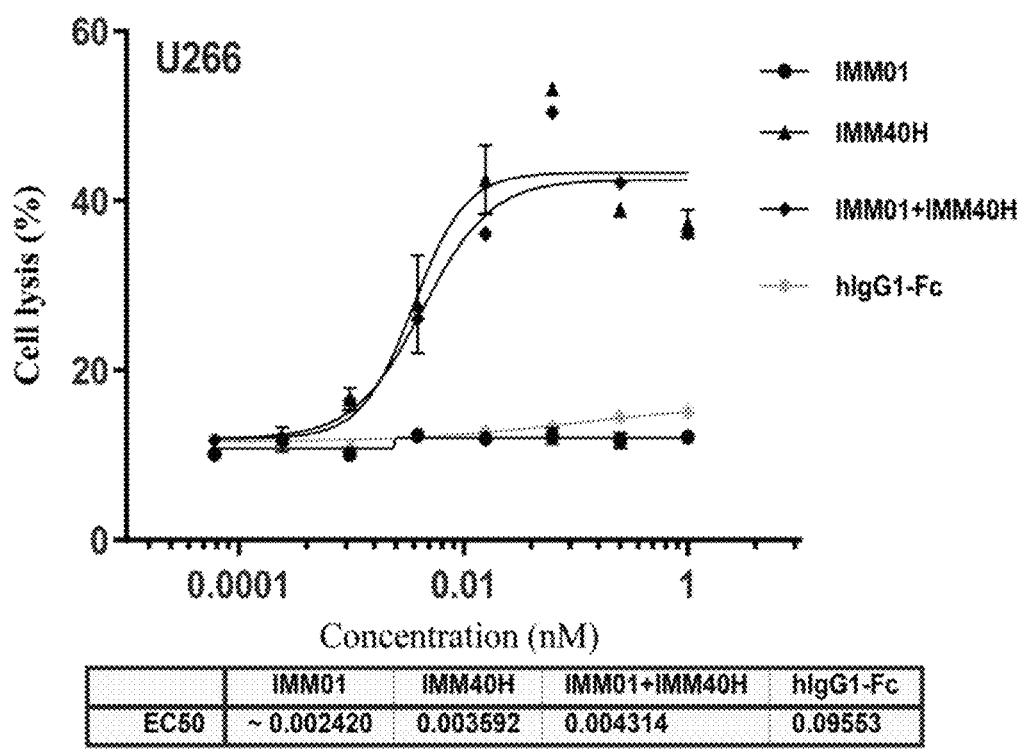
Figure 5C:
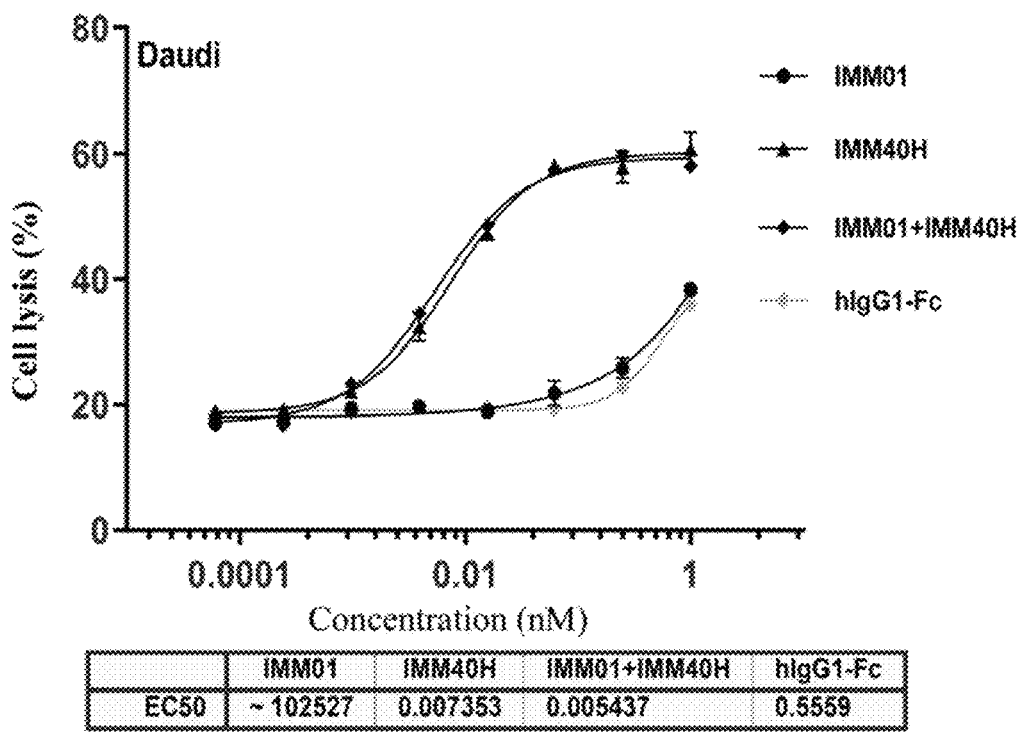
Figure 5D:
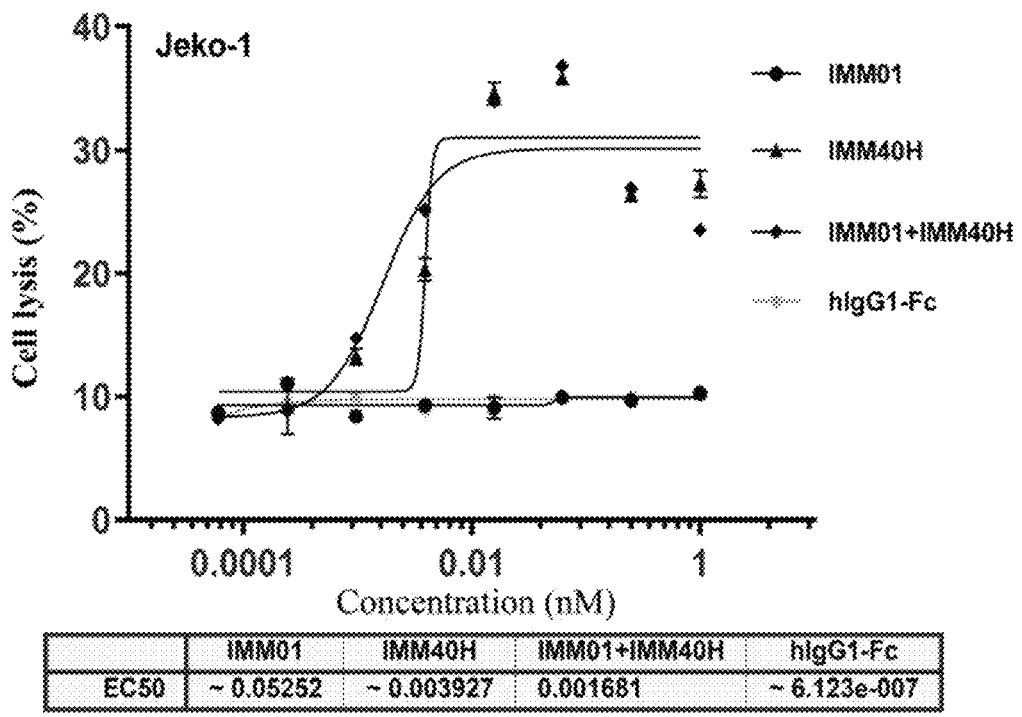

Similarly, as shown in FIG. 5B-5D, the ADCC against CD47+CD70+ U266 cells, CD47+CD70+ Daudi cells, and CD47+CD70+ Jeko-1 cells induced by IMM40H was similar to that induced by the IMM40H+IMM01 mixture, but much higher than that induced by IMM01.

Example 6. Exemplary Antibody Induced High Antibody-Dependent Cellular Phagocytosis (ADCP) Against CD70+ Cells Macrophages (THP-1) were digested with 0.25% trypsin for 2 min at 37° C., re-suspended in complete culture medium (1640+10% FBS), centrifuged at 1000 rpm for 5 min, collected, and added to a 96-well plate. The plate contained 3×10$^5$ THP-1 cells in 100 µl complete medium with 200 ng/ml PMA in each well and incubated overnight.

CFSE (Cat #21888-25 mg, Sigma) at 1 mM was 1:500 diluted and used to label tumor cells, including CD70+ CD47+ Raji cells, U266 cells, Daudi cells and Jeko-1 cells.

The CFSE-labeled tumor cells in 100 µl complete media at 1×10$^6$/ml, were mixed with 100 µl serially diluted IMM40H, IMM01, the IMM40H+IMM01 mixture, and hIgG-Fc (for the IMM40H+IMM01 mixture, the initial concentrations of IMM40H and IMM01 were the same as those in the single protein group), respectively, and cultured in an incubator for 45 min.

The supernatants were removed from the plate where THP-1 cells were cultured, and the plate was added with 200 µl of the tumor cell/protein mixtures in each well and incubated in the incubator for 2 hours. The test was done in duplicate, and contained control groups with THP-1 cells alone, and THP-1 plus tumor cells without CD70 or CD47 targeting proteins.

The plate was washed for five times with PBS, to remove free floating CFSE-labeled tumor cells. Then, the plate was added with 200 µl PBS to re-suspend THP-1 cells, and the THP-1 cells were measured for fluorescence intensity in a flow cytometer, which indicated the THP-1 cells' phagocytosis activity.

Figure 6A:
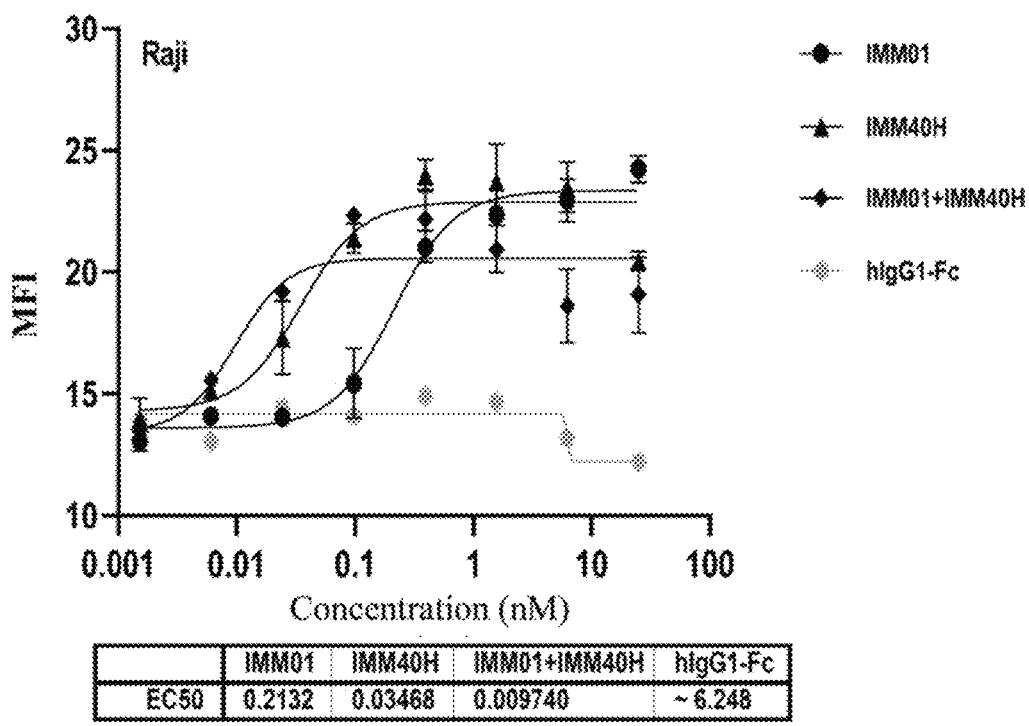
FIGS. 6A to 6D show the abilities of IMM40H and IMM40H+IMM01 to induce antibody dependent cellular phagocytosis (ADCP) against CD47$^+$CD70$^+$ Raji cells (A), CD47$^+$CD70$^+$ U266 cells (B), CD47$^+$CD70$^+$ Daudi cells (C) and CD47$^+$CD70$^+$ Jeko-1 cells (D), with IMM01 and hIgG1-Fc used as the controls.

According to FIG. 6A, the ADCP against CD47+CD70+ Raji cells induced by IMM40H was much higher than that induced by IMM01 as well as the IMM01+IMM40H mixture (at high concentrations).

Figure 6B:
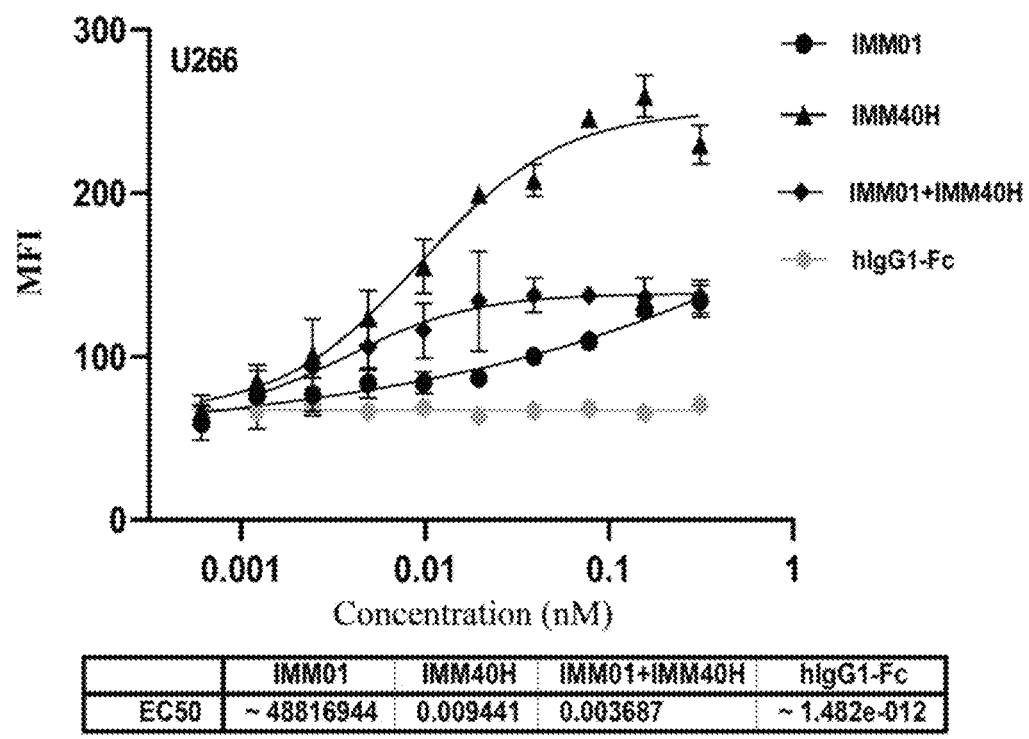

As shown in FIG. 6B, the ADCP against CD47+CD70+ U266 cells induced by IMM40H was much higher than those induced by IMM01 and the IMM01+IMM40H mixture.

Figure 6C:
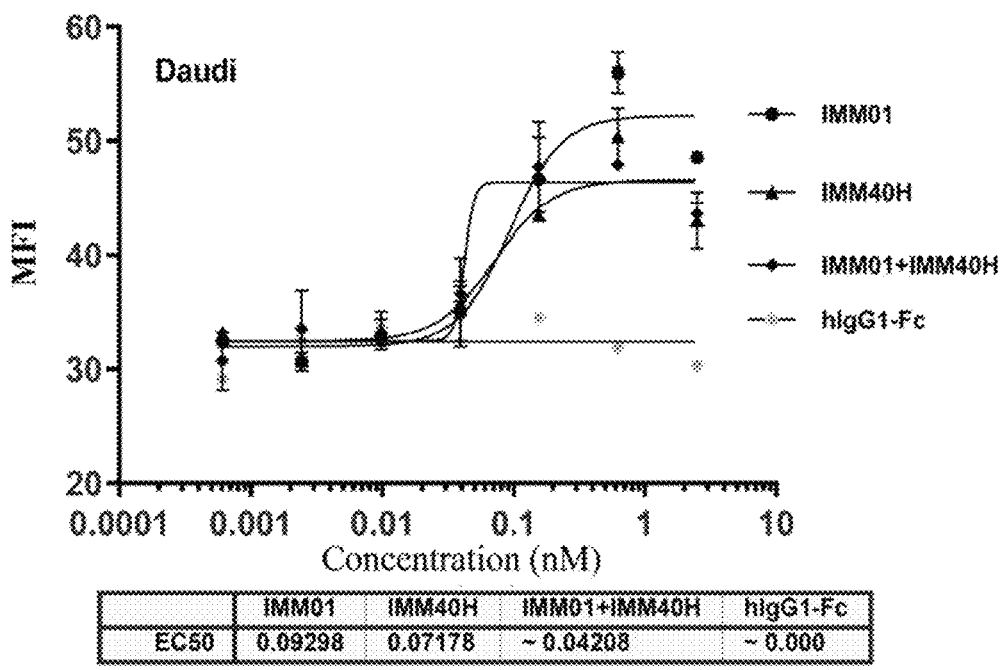

According to FIG. 6C, the ADCP against CD47+CD70+ Daudi cells induced by IMM40H was comparable to those induced by IMM01 and the IMM01+IMM04H mixture.

Figure 6D:
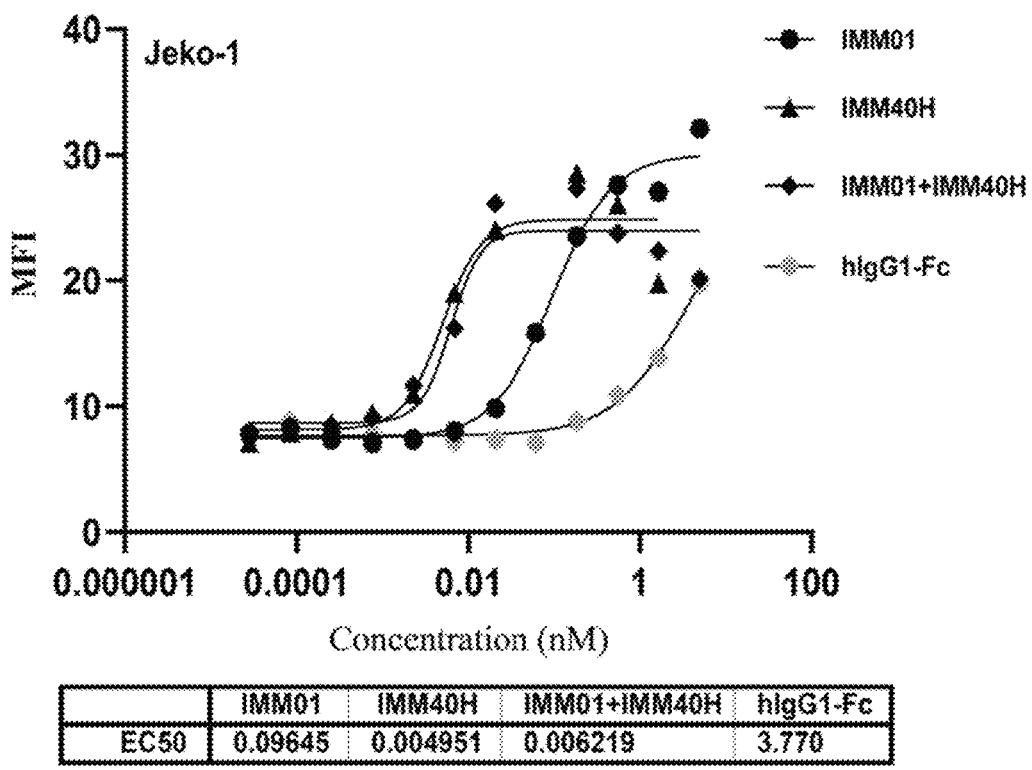

Further, it can be seen from FIG. 6D that IMM40H induced ADCP against CD47+CD70+ Jeko-1 cells, and the ADCP level was comparable to that induced by the IMM01+ IMM40H mixture, and much higher than that induced by IMM01.

Example 7. Exemplary Antibody Induced High Complement Dependent Cytotoxicity (CDC) Against CD70+ Cells CD70+CD47+ Raji cells in 50 µl serum-free medium at a density of 3×10$^5$/ml, were seeded onto a 96-well U-shaped cell culture plate, and incubated with 30 µl serially diluted IMM01, IMM40H, the IMM01+IMM40H mixture and hIgG1-Fc (4-fold diluted with a starting concentration at 25 nM, for the IMM01+IMM40H mixture, IMM01 and IMM40H both had the starting concentration at 25 nM), respectively, for 30 min. The plate was added with 20 µl 1:13 diluted rabbit complement (Cat #CL3111, Accurate Chemical), and incubated for 4 hrs. Then, the plate was added with propidium iodide (PI) (Cat #P4170, Sigma) at a concentration of 5 µg/ml, and then subjected to FACS analysis for PI signals, based on which percent cell lysis was determined.

Figure 7:
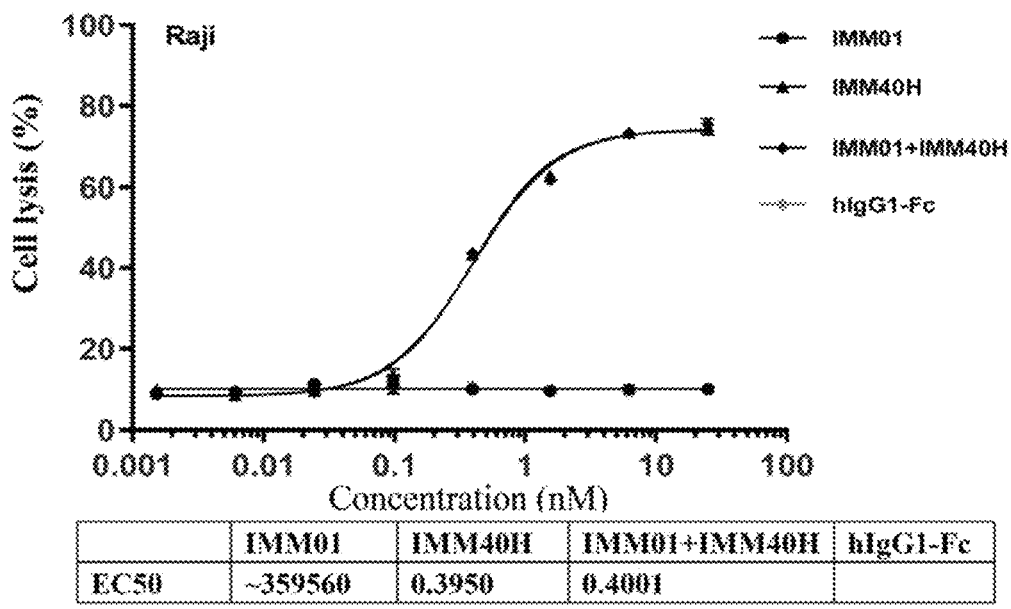
FIG. 7 shows the abilities of IMM40H and IMM40H+IMM01 to induce complement dependent cytotoxicity (CDC) against CD47$^+$CD70$^+$ Raji cells, with hIgG1-Fc and IMM01 used as the controls.

As shown in FIG. 7, IMM40H induced high CDC against CD70+ CD47+ Raji cells, which was comparable to that induced by the IMM01+IMM40H mixture, and much higher than that induced by IMM01.

Example 8. Exemplary Antibody Showed Potent In Vivo Anti-Tumor Activity

Thirty 5-6-week-old SCID mice were each injected at the back close to the right axilla with a mixture of 5×10$^6$ U266 cells in 100 µl culture medium and 100 µl Matrigel matrix. When tumor sizes reached ~200 mm$^3$, the mice were randomly allocated into 5 groups with 6 mice per group, and this day was designated as Day 0. From that day on, mice were respectively given intraperitoneal injection of PBS, IMM40H (0.3 mg/kg), IMM40H (1.0 mg/kg), IMM01 (0.5 mg/kg), and IMM01 (0.5 mg/kg)+IMM40H (1.0 mg/kg), for 4 weeks, once per week. Administration was stopped at the end of week 4, and mice were observed for another 3.5 weeks. Mice tumor sizes and body weights were measured every 3-4 days.

The tumor volume (V) was calculated as (length×width$^2$)/ 2. Relative tumor volume (RTV)=$V_t/V_0$, wherein $V_t$ referred to the tumor size at Day t (Dt), and $V_0$ referred to the tumor size at Day 0 (D0).

Tumor growth inhibition rate (TGI) was calculated by the formula: TGI (%)=(1−tumor volume change in administration group/tumor volume change in vehicle control group)× 100%.

The test regime and results were summarized in Table 1.

TABLE 1

Anti-tumor effects of IMM40H and other agents at D52

| Group | Drug | Animal # | Dose (mg/kg) | Treatment | TGI | P value |
|---|---|---|---|---|---|---|
| 1 | PBS | 6 | n/a | i.p.q.w. × 4 | | |
| 2 | IMM40H | 6 | 0.3 | i.p.q.w. × 4 | 82.66% | <0.01 |
| 3 | IMM40H | 6 | 1.0 | i.p.q.w. × 4 | 100% | <0.01 |
| 4 | IMM01 | 6 | 0.5 | i.p.q.w. × 4 | 100% | <0.01 |
| 5 | IMM01 + IMM40H | 6 | 0.5 + 1.0 | i.p.q.w. × 4 | 100% | <0.01 |

Figure 8:
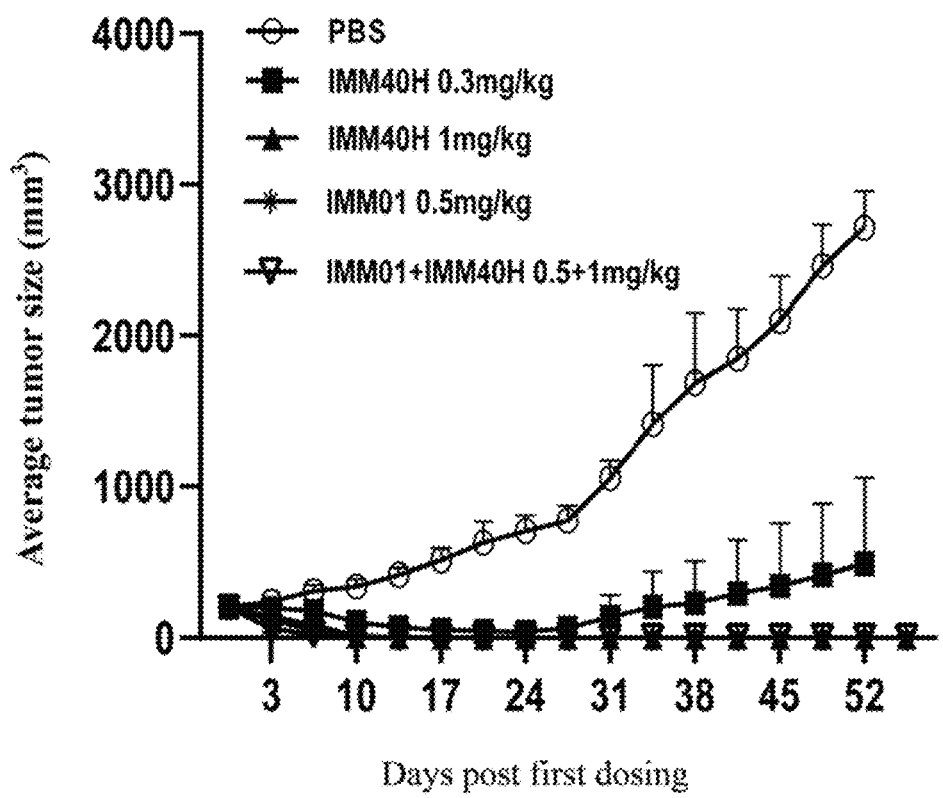
FIG. 8 shows the in vivo anti-tumor efficacy of IMM40H and IMM40H+IMM01 in a U266 xenograft SCID mice model.

The results were shown in FIG. 8 and Table 1. On Day 52 (D52), the average tumor volume in Group 1 (PBS) was 2715.13±107.27 mm$^3$, with the average RTV being 14.01±0.67.

After treatment with IMM40H at 0.3 mg/kg for four weeks, the tumor size at Day 28 (D28) was 61.42±27.64 mm$^3$, and RTV was 0.30±0.13. The tumor size and the RTV significantly decreased during D3 to D28 compared to the vehicle control group ($p<0.05$). On Day 52, the average tumor size and RTV became 487.78±233.37 mm$^3$ and 2.43±1.16, respectively. Compared to the vehicle control group, the tumor size and the RTV continued to decrease ($p<0.01$) after the administration was stopped.

In the IMM40H (1.0 mg/kg), IMM01 (0.5 mg/kg), and IMM01+IMM40H (0.5 mg/kg+1.0 mg/kg) groups, the tumor sizes at Day 28 were all 0.00±0.00 mm$^3$, and the RTVs were all 0.00±0.00. The tumor size and the RTV significantly decreased during D3 to D28 compared to the vehicle control group ($p<0.01$). On Day 52, the average tumor size and RTV in each of these groups were 0.00±0.00 mm$^3$ and 0.00±0.00, respectively. Compared to the vehicle control group, the tumor size and the RTV continued to decrease ($p<0.01$) after the administration was stopped.

The data suggested IMM40H had potent anti-tumor effects, the tumors were completely removed at the dose of 1.0 mg/kg.

The sequences of the application were set forth below.

| 描述/序列 | SEQ ID NO. |
|---|---|

HV-CDR1 of IMM40C, IMM40H and IMM40M
(SEQ ID NO: 1)
GYTFTDSA

HV-CDR2 of IMM40C, IMM40H and IMM40M
(SEQ ID NO: 2)
ISTYDGDT

HV-CDR3 of IMM40C, IMM40H and IMM40M
(SEQ ID NO: 3)
ARRGYYDYDWFPY

LV-CDR1 of IMM40C, IMM40H and IMM40M
(SEQ ID NO: 4)
KSVSASGYSF

LV-CDR2 of IMM40C, IMM40H and IMM40M
(SEQ ID NO: 5)
LAS

LV-CDR3 of IMM40C, IMM40H and IMM40M
(SEQ ID NO: 6)
QHSRELPPT

Heavy chain variable region of IMM40C
(SEQ ID NO: 7)
QVQLQQSGPEVVRPGVSVKISCKGSGYTFTDSALHWVKQSHAKSLEWIGV
ISTYDGDTDYNQKFKGKATMTVDKSSSTAYMELARLTSEDSAIYYCARRG
YYDYDWFPYWGQGTLVTVSA Light chain variable region of IMM40C
(SEQ ID NO: 8)
DIVLTQSPASLAISLGQRATISCRASKSVSASGYSFLHWYQQKPGQPPKL
LIYLASNLESGVPARFSGSGSGTDFTLNIHPVEEEDAATFYCQHSRELPP
TFGGGTKLEIK Heavy chain variable region of IMM40H and IMM40M
(SEQ ID NO: 9)
QVQLVQSGAEVKKPGASVKVSCKVSGYTFTDSALHWVRQAPGKGLEWMGV
ISTYDGDTDYNQKFKGRVTMTEDTSTDTAYMELSSLRSEDTAVYYCARRG
YYDYDWFPYWGQGTLVTVSA Light chain variable region of IMM40H
(SEQ ID NO: 10)
DIVLTQSPASLAVSPGQRATITCRASKSVSASGYSFLHWYQQKPGQPPKL
LIYLASNLESGVPARFSGSGSGTDFTLTINPVEAXDTANYYCQHSRELPP
TFGGGTKVEIK
X = N DIVLTQSPASLAVSPGQRATITCRASKSVSASGYSFLHWYQQKPGQPPKL
LIYLASNLESGVPARFSGSGSGTDFTLTINPVEANDTANYYCQHSRELPP
TFGGGTKVEIK Light chain variable region of IMM40M
SEQ ID NO: 10
DIVLTQSPASLAVSPGQRATITCRASKSVSASGYSFLHWYQQKPGQPPKL
LIYLASNLESGVPARFSGSGSGTDFTLTINPVEAEDTANYYCQHSRELPP
TFGGGTKVEIK,
X = E Heavy chain constant region
(SEQ ID NO: 11)
ASTKGPSVFPLAPSSKSTSGGTAALGCLVKDYFPEPVTVSWNSGALTSGV
HTFPAVLQSSGLYSLSSVVTVPSSSLGTQTYICNVNHKPSNTKVDKRVEP
KSCDKTHTCPPCPAPELLGGPSVFLFPPKPKDTLMISRTPEVTCVVVDVS
HEDPEVKFNWYVDGVEVHNAKTKPREEQYNATYRVVSVLTVLHQDWLNGK
EYKCKVSNKALPAPIEKTISKAKGQPREPQVYTLPPSREEMTKNQVSLTC
LVKGFYPSDIAVEWESNGQPENNYKTTPPVLDSDGSFFLYSKLTVDKSRW
QQGNVFSCSVMHEALHNHYTQKSLSLSPGK Light chain constant region
(SEQ ID NO: 12)
RTVAAPSVFIFPPSDEQLKSGTASVVCLLNNFYPREAKVQWKVDNALQSG
NSQESVTEQDSKDSTYSLSSTLTLSKADYEKHKVYACEVTHQGLSSPVTK
SFNRGEC IMM40C's heavy chain
(SEQ ID NO: 13)
ATGGGTTGGAGCTGTATCATCTTCTTTCTGGTAGCAACAGCTACAGGTGT
GCACTCCCAGGTCCAGCTGCAGCAGTCTGGGCCTGAGGTGGTGAGGCCTG
GGGTCTCAGTGAAGATTTCCTGCAAGGGTTCCGGCTACACATTCACTGAT
AGTGCTTTGCACTGGGTGAAGCAGAGTCATGCAAAGAGTCTAGAGTGGAT
TGGAGTTATTAGTACTTACGATGGTGATACAGACTACAACCAGAAGTTTA
AGGGCAAGGCCACAATGACTGTAGACAAATCCTCCAGCACAGCCTATATG
GAACTTGCCAGATTGACATCTGAGGATTCTGCCATCTATTACTGTGCAAG
AAGGGGATACTATGATTACGACTGGTTTCCTTACTGGGGCCAAGGGACTC
TGGTCACTGTCTCTGCAGCTAGCACCAAGGGCCCATCGGTCTTCCCCCTG
GCACCCTCCTCCAAGAGCACCTCTGGGGGCACAGCGGCCCTGGGCTGCCT
GGTCAAGGACTACTTCCCCGAACCGGTGACGGTGTCGTGGAACTCAGGCG
CCCTGACCAGCGGCGTGCACACCTTCCCGGCTGTCCTACAGTCCTCAGGA
CTCTACTCCCTCAGCAGCGTGGTGACCGTGCCCTCCAGCAGCTTGGGCAC
CCAGACCTACATCTGCAACGTGAATCACAAGCCCAGCAACACCAAGGTGG
ACAAGAGAGTTGAGCCCAAATCTTGTGACAAAACTCACACATGCCCACCG
TGCCCAGCACCTGAACTCCTGGGGGGACCGTCAGTCTTCCTCTTCCCCCC
AAAACCCAAGGACACCCTCATGATCTCCCGGACCCCTGAGGTCACATGCG
TGGTGGTGGACGTGAGCCACGAAGACCCTGAGGTCAAGTTCAACTGGTAT
GTGGACGGCGTGGAGGTGCATAATGCCAAGACAAAGCCGCGGGAGGAGCA
GTACAACGCCACGTACCGTGTGGTCAGCGTCCTCACCGTCCTGCACCAAG
ACTGGCTGAATGGCAAGGAGTACAAGTGCAAGGTCTCCAACAAAGCCCTC
CCAGCCCCCATCGCCGCAACCATCTCCAAAGCCAAAGGGCAGCCCCGAGA
ACCACAGGTGTACACCCTGCCCCCATCCCGGGAGGAGATGACCAAGAACC

描述/
序列/SEQ ID NO.

AAGTCAGCCTGACCTGCCTGGTCAAAGGCTTCTATCCCAGCGACATCGCC
GTGGAGTGGGAGAGCAATGGGCAGCCGGAGAACAACTACAAGACCACGCC
TCCCGTGCTGGACTCCGACGGCTCCTTCTTCCTCTATTCCAAGCTCACCG
TGGACAAGAGCAGGTGGCAGCAGGGGAACGTCTTCTCATGCTCCGTGATG
CATGAGGCTCTGCACAACCACTACACGCAGAAGAGCCTCTCCCTGTCTCC
GGGCAAATGA

IMM40C's light chain
(SEQ ID NO: 14)
ATGGAGACAGACACACTCCTGTTATGGGTACTGCTGCTCTGGGTTCCAGG
TTCCACTGGTGACATTGTGCTGACACAGTCTCCTGCTTCCTTAGCTATAT
CTCTGGGGCAGAGGGCCACCATCTCATGCAGGGCCAGCAAAAGTGTCAGT
GCATCTGGCTATAGTTTTCTGCACTGGTACCAACAGAAACAGGACAGCC
ACCCAAACTCCTCATCTATCTTGCATCCAACCTCGAATCTGGGGTCCCTG
CCAGGTTCAGTGGCAGTGGGTCTGGGACAGACTTTACCCTCAACATCCAT
CCTGTGGAGGAGGAGGATGCTGCAACCTTTTACTGTCAGCACAGTAGGGA
GCTTCCTCCGACGTTCGGTGGAGGCACCAAACTGGAAATCAAACGTGAGT
TCTAGAGGATCCATCTGGGATAAGCATGCTGTTTTCTGTCTGTCCCTAAC
ATGCCCTGTGATTATCCGCAAACAACACACCCAAGGGCAGAACTTTGTTA
CTTAAACACCATCCTGTTTGCTTCTTTCCTCAGGAACTGTGGCTGCACCA
TCTGTCTTCATCTTCCCGCCATCTGATGAGCAGTTGAAATCTGGAACTGC
CTCTGTTGTGTGCCTGCTGAATAACTTCTATCCCAGAGAGGCCAAAGTAC
AGTGGAAGGTGGATAACGCCCTCCAATCGGGTAACTCCCAGGAGAGTGTC
ACAGAGCAGGACAGCAAGGACAGCACCTACAGCCTCAGCAGCACCCTGAC
GCTGAGCAAAGCAGACTACGAGAAACACAAAGTCTACGCCTGCGAAGTCA
CCCATCAGGGCCTGAGCTCGCCCGTCACAAAGAGCTTCAACAGGGGAGAG
TGTTAG IMM40H/IMM40M's heavy chain
(SEQ ID NO: 15)
ATGGGATGGTCATGTATCATCCTTTTTCTGGTAGCAACTGCAACTGGAGT
ACATTCACAAGTGCAGCTGGTGCAGAGCGGCGCCGAGGTGAAGAAGCCTG
GCGCAAGCGTGAAGGTGAGCTGCAAGGTGAGCGGCTACACCTTCACCGAC
AGCGCCCTGCACTGGGTGAGACAAGCCCCTGGCAAGGGCCTGGAGTGGAT
GGGCGTGATCAGCACCTACGACGGCGACACCGACTACAATCAGAAGTTCA
AGGGCAGAGTGACCATGACCGAGGACACAAGCACCGACACCGCCTACATG
GAGCTGAGCAGCCTGAGAGCGGAGGACACCGCCGTGTACTACTGCGCTAG
AAGAGGCTACTACGACTACGACTGGTTCCCTTACTGGGGACAAGGCACCC
TGGTGACCGTGAGCGCCGCTAGCACCAAGGGCCCATCGGTCTTCCCCCTG
GCACCCTCCTCAAGAGCACCTCTGGGGGCACAGCGGCCCTGGGCTGCCT
GGTCAAGGACTACTTCCCCGAACCGGTGACGGTGTCGTGGAACTCAGGCG
CCCTGACCAGCGGCGTGCACACCTTCCCGGCTGTCCTACAGTCCTCAGGA
CTCTACTCCCTCAGCAGCGTGGTGACCGTGCCCTCCAGCAGCTTGGGCAC
CCAGACCTACATCTGCAACGTGAATCACAAGCCCAGCAACACCAAGGTGG
ACAAGAGAGTTGAGCCCAAATCTTGTGACAAAACTCACACATGCCCACCG
TGCCCAGCACCTGAACTCCTGGGGGGACCGTCAGTCTTCCTCTTCCCCCC
AAAACCCAAGGACACCCTCATGATCTCCCGGACCCCTGAGGTCACATGCG
TGGTGGTGGACGTGAGCCACGAAGACCCTGAGGTCAAGTTCAACTGGTAT
GTGGACGGCGTGGAGGTGCATAATGCCAAGACAAAGCCGCGGGAGGAGCA
GTACAACGCCACGTACCGTGTGGTCAGCGTCCTCACCGTCCTGCACCAAG
ACTGGCTGAATGGCAAGGAGTACAAGTGCAAGGTCTCCAACAAAGCCCTC
CCAGCCCCCATCGCCGCAACCATCTCCAAAGCCAAAGGGCAGCCCCGAGA
ACCACAGGTGTACACCCTGCCCCCATCCCGGGAGGAGATGACCAAGAACC
AAGTCAGCCTGACCTGCCTGGTCAAAGGCTTCTATCCCAGCGACATCGCC
GTGGAGTGGGAGAGCAATGGGCAGCCGGAGAACAACTACAAGACCACGCC
TCCCGTGCTGGACTCCGACGGCTCCTTCTTCCTCTATTCCAAGCTCACCG
TGGACAAGAGCAGGTGGCAGCAGGGGAACGTCTTCTCATGCTCCGTGATG
CATGAGGCTCTGCACAACCACTACACGCAGAAGAGCCTCTCCCTGTCTCC
GGGCAAATGA IMM40H's light chain
(SEQ ID NO: 16)
ATGGGATGGTCATGTATCATCCTTTTTCTGGTAGCAACTGCAACTGGAGT
ACATTCAGACATCGTGCTGACACAGAGCCCTGCAAGCCTGGCCGTGAGCC
CTGGACAGAGAGCCACCATCACCTGCAGAGCAAGCAAGAGCGTGAGCGCA
AGCGGCTACAGCTTCCTGCACTGGTATCAGCAGAAGCCTGGACAGCCTCC
TAAGCTGCTGATCTACCTGGCAAGCAACCTGGAGAGCGGCGTGCCTGCTA
GATTCAGCGGCAGCGGCAGCGGCACCGACTTCACCCTGACCATCAACCCT
GTGGAGGCCN1AN2GACACCGCCAACTACTACTGTCAGCACAGCAGAGAG
CTGCCTCCTACCTTCGGCGGCGGCACCAAGGTGGAGATCAAGCGTGAGTT
CTAGAGGATCCATCTGGGATAAGCATGCTGTTTTCTGTCTGTCCCTAACA
TGCCCTGTGATTATCCGCAAACAACACACCCAAGGGCAGAACTTTGTTACT
TAAACACCATCCTGTTTGCTTCTTTCCTCAGGAACTGTGGCTGCACCATC
TGTCTTCATCTTCCCGCCATCTGATGAGCAGTTGAAATCTGGAACTGCCT
CTGTTGTGTGCCTGCTGAATAACTTCTATCCCAGAGAGGCCAAAGTACA
GTGGAAGGTGGATAACGCCCTCCAATCGGGTAACTCCCAGGAGAGTGTCA CAGAGCAGGACAGCAAGGACAGCACCTACAGCCTCAGCAGCACCCTGACG
CTGAGCAAAGCAGACTACGAGAAACACAAAGTCTACGCCTGCGAAGTCAC
CCATCAGGGCCTGAGCTCGCCCGTCACAAAGAGCTTCAACAGGGGAGAGT
GTTAG
N1 = A, N2 = C ATGGGATGGTCATGTATCATCCTTTTTCTGGTAGCAACTGCAACTGGAGT
ACATTCAGACATCGTGCTGACACAGAGCCCTGCAAGCCTGGCCGTGAGCC
CTGGACAGAGAGCCACCATCACCTGCAGAGCAAGCAAGAGCGTGAGCGCA
AGCGGCTACAGCTTCCTGCACTGGTATCAGCAGAAGCCTGGACAGCCTCC
TAAGCTGCTGATCTACCTGGCAAGCAACCTGGAGAGCGGCGTGCCTGCTA
GATTCAGCGGCAGCGGCAGCGGCACCGACTTCACCCTGACCATCAACCCT
GTGGAGGCCAACACCGCCAACTACTACTGTCAGCACAGCAGAGAGAGCT
GCCTCCTACCTTCGGCGGCGGCACCAAGGTGGAGATCAAGCGTGAGTTCT
AGAGGATCCATCTGGGATAAGCATGCTGTTTTCTGTCTGTCCCTAACATG
CCCTGTGATTATCCGCAAACAACACACCCAAGGGCAGAACTTTGTTACTT
AAACACCATCCTGTTTGCTTCTTTCCTCAGGAACTGTGGCTGCACCATCT
GTCTTCATCTTCCCGCCATCTGATGAGCAGTTGAAATCTGGAACTGCCTC
TGTTGTGTGCCTGCTGAATAACTTCTATCCCAGAGAGGCCAAAGTACAGT
GGAAGGTGGATAACGCCCTCCAATCGGGTAACTCCCAGGAGAGTGTCACA
GAGCAGGACAGCAAGGACAGCACCTACAGCCTCAGCAGCACCCTGACGCT
GAGCAAAGCAGACTACGAGAAACACAAAGTCTACGCCTGCGAAGTCACCC
ATCAGGGCCTGAGCTCGCCCGTCACAAAGAGCTTCAACAGGGGAGAGTGT
TAG IMM40M's light chain
SEQ ID NO: 16
ATGGGATGGTCATGTATCATCCTTTTTCTGGTAGCAACTGCAACTGGAGT
ACATTCAGACATCGTGCTGACACAGAGCCCTGCAAGCCTGGCCGTGAGCC
CTGGACAGAGAGCCACCATCACCTGCAGAGCAAGCAAGAGCGTGAGCGCA
AGCGGCTACAGCTTCCTGCACTGGTATCAGCAGAAGCCTGGACAGCCTCC
TAAGCTGCTGATCTACCTGGCAAGCAACCTGGAGAGCGGCGTGCCTGCTA
GATTCAGCGGCAGCGGCAGCGGCACCGACTTCACCCTGACCATCAACCCT
GTGGAGGCCGAAGACACCGCCAACTACTACTGTCAGCACAGCAGAGAGCT
GCCTCCTACCTTCGGCGGCGGCACCAAGGTGGAGATCAAGCGTGAGTTCT
AGAGGATCCATCTGGGATAAGCATGCTGTTTTCTGTCTGTCCCTAACATG
CCCTGTGATTATCCGCAAACAACACACCCAAGGGCAGAACTTTGTTACTT
AAACACCATCCTGTTTGCTTCTTTCCTCAGGAACTGTGGCTGCACCATCT
GTCTTCATCTTCCCGCCATCTGATGAGCAGTTGAAATCTGGAACTGCCTC
TGTTGTGTGCCTGCTGAATAACTTCTATCCCAGAGAGGCCAAAGTACAGT
GGAAGGTGGATAACGCCCTCCAATCGGGTAACTCCCAGGAGAGTGTCACA
GAGCAGGACAGCAAGGACAGCACCTACAGCCTCAGCAGCACCCTGACGCT
GAGCAAAGCAGACTACGAGAAACACAAAGTCTACGCCTGCGAAGTCACCC
ATCAGGGCCTGAGCTCGCCCGTCACAAAGAGCTTCAACAGGGGAGAGTGT
TAG,
N1 = G, N2 = A SIRPalphaD1 mutant-Fc (IMM01)
(SEQ ID NO: 17)
EEELQVIQPDKSVSVAAGESAILHCTVTSLIPVGPIQWFRGAGPARELIY
NQKEGHFPRVTTVSESTKRENMDFSISISAITPADAGTYYCVKFRKGSPD
TEFKSGAGTELSVRAKPSAPVVSGPAARATPQHEPKSCDKTHTCPPCPAP
ELLGGPSVFLFPPKPKDTLMISRTPEVTCVVVDVSHEDPEVKFNWYVDGV
EVHNAKTKPREEQYNSTYRVVSVLTVLHQDWLNGKEYKCKVSNKALPAPI
EKTISKAKGQPREPQVYTLPPSRDELTKNQVSLTCLVKGFYPSDIAVEWE
SNGQPENNYKTTPPVLDSDGSFFLYSKLTVDKSRWQQGNVFSCSVMHEAL
HNHYTQKSLSLSPG Signal peptide of murine IgG1 heavy chain
(SEQ ID NO: 18)
ATGGGATGGTCATGTATCATCCTTTTTCTGGTAGCAACTGCAACTGGAGT
ACATTCA Kozak
(SEQ ID NO: 19)
GCCGCCACC Cusatuzumab's heavy chain
(SEQ ID NO: 20)
MGWSCIILFLVATATGVHSEVQLVESGGGLVQPGGSLRLSCAASGFTFSV
YYMNWVRQAPGKGLEWVSDINNEGGTTYYADSVKGRFTISRDNSKNSLYL
QMNSLRAEDTAVYYCARDAGYSNHVPIFDSWGQGTLVTVSSASTKGPSVF
PLAPSSKSTSGGTAALGCLVKDYFPEPVTVSWNSGALTSGVHTFPAVLQS
SGLYSLSSVVTVPSSSLGTQTYICNVNHKPSNTKVDKKVEPKSCDKTHTC
PPCPAPELLGGPSVFLFPPKPKDTLMISRTPEVTCVVVDVSHEDPEVKFN
WYVDGVEVHNAKTKPREEQYNSTYRVVSVLTVLHQDWLNGKEYKCKVSNK

| 描述/序列/SEQ ID NO. |
|---|
| ALPAPIEKTISKAKGQPREPQVYTLPPSRDELTKNQVSLTCLVKGFYPSD<br>IAVEWESNGQPENNYKTTPPVLDSDGSFFLYSKLTVDKSRWQQGNVFSCS<br>VMHEALHNHYTQKSLSLSPGK |
| Cusatuzumab's light chain<br>(SEQ ID NO: 21)<br>MGWSCIILFLVATATGVHSQAVVTQEPSLTVSPGGTVTLTCGLKSGSVTS<br>DNFPTWYQQTPGQAPRLLIYNTNTRHSGVPDRFSGSILGNKAALTITGAQ<br>ADDEAEYFCALFISNPSVEFGGGTQLTVLGQPKAAPSVTLFPPSSEELQA<br>NKATLVCLISDFYPGAVTVAWKADSSPVKAGVETTTPSKQSNNKYAASSY<br>LSLTPEQWKSHRSYSCQVTHEGSTVEKTVAPTECS |
| CD27(ECD)-Fc<br>(SEQ ID NO: 22)<br>ATPAPKSCPERHYWAQGKLCCQMCEPGTFLVKDCDQHRKAAQCDPCIPGV<br>SFSPDHHTRPHCESCRHCNSGLLVRNCTITANAECACRNGWQCRDKECTE<br>CDPLPNPSLTARSSQALSPHPQPTHLPYVSEMLEARTAGHMQTLADFRQL<br>PARTLSTHWPPQRSLCSSDFIREFEPKSCDKTHTCPPCPAPELLGGPSVF<br>LFPPKPKDTLMISRTPEVTCVVVDVSHEDPEVKFNWYVDGVEVHNAKTKP<br>REEQYNSTYRVVSVLTVLHQDWLNGKEYKCKVSNKALPAPIEKTISKAKG<br>QPREPQVYTLPPSRDELTKNQVSLTCLVKGFYPSDIAVEWESNGQPENNY<br>KTTPPVLDSDGSFFLYSKLTVDKSRWQQGNVFSCSVMHEALHNHYTQKSL<br>SLSPGK |
| CD27-CAR<br>(SEQ ID NO: 23)<br>ATPAPKSCPERHYWAQGKLCCQMCEPGTFLVKDCDQHRKAAQCDPCIPGV<br>SFSPDHHTRPHCESCRHCNSGLLVRNCTITANAECACRNGWQCRDKECTE<br>CDPLPNPSLTARSSQALSPHPQPTHLPYVSEMLEARTAGHMQTLADFRQL<br>PARTLSTHWPPQRSLCSSDFIRTTTPAPRPPTPAPTIASQPLSLRPEACR<br>PAAGGAVHTRGLDFACDFWVLVVVGGVLACYSLLVTVAFIIFWVRSKRSR<br>LLHSDYMNMTPRRPGPTRKHYQPYAPPRDFAAYRSRVKFSRSAEPPAYQQ<br>GQNQLYNELNLGRREEYDVLDKRRGRDPEMGGKPRRKNPQEGLYNELQKD<br>KMAEAYSEIGMKGERRRGKGHDGLYQGLSTATKDTYDALHMQALPPR |

While the application has been described above in connection with one or more embodiments, it should be understood that the application is not limited to those embodiments, and the description is intended to cover all alternatives, modifications, and equivalents, as may be included within the spirit and scope of the appended claims. All referenced cited herein are further incorporated by reference in their entirety.

REFERENCES

A. Agathanggelou, G. Niedobitek, R. Chen, J. Nicholls, W. Yin, L. S. Young, Expression of immune regulatory molecules in Epstein-Barr virus-associated nasopharyngeal carcinomas with prominent lymphoid stroma. Evidence for a functional interaction between epithelial tumor cells and infiltrating lymphoid cells, The American journal of pathology, 147 (1995) 1152.

A. W. Ho, E. Hatjiharissi, B. T. Ciccarelli, A. R. Branagan, Z. R. Hunter, X. Leleu, O. Tournilhac, L. Xu, K. O'Connor, R. J. Manning, CD27-CD70 interactions in the pathogenesis of Waldenström macroglobulinemia, Blood, The Journal of the American Society of Hematology, 112 (2008) 4683-4689.

B. F. Israel, M. Gulley, S. Elmore, S. Ferrini, W.-h. Feng, S. C. Kenney, Anti-CD70 antibodies: a potential treatment for EBV+CD70-expressing lymphomas, Molecular cancer therapeutics, 4 (2005) 2037-2044.

Bobby Kwanghoon Han, Nancy J Olsen, Andrea Bottaro. Semin Arthritis Rheum, The CD27-CD70 pathway and pathogenesis of autoimmune disease. 2016 February; 45(4):496-501

C. L. Law, K. A. Gordon, B. E. Toki, A. K. Yamane, M. A. Hering, C. G. Cerveny, J. M. Petroziello, M. C. Ryan, L. Smith, R. Simon, Lymphocyte activation antigen CD70 expressed by renal cell carcinoma is a potential therapeutic target for anti-CD70 antibody-drug conjugates, Cancer Research, 66 (2006) 2328-2337.

C. Pich, G. Sarrabayrouse, I. Teiti, B. Mariamé, P. Rochaix, L. Lamant, G. Favre, V. Maisongrosse, A.-F. Tilkin-Mariamé, Melanoma-expressed CD70 is involved in invasion and metastasis, British journal of cancer, 114 (2016) 63-70.

C. Riether, C. M. Schürch, E. D. Bührer, M. Hinterbrandner, A.-L. Huguenin, S. Hoepner, I. Zlobec, T. Pabst, R. Radpour, A. F. Ochsenbein, CD70/CD27 signaling promotes blast stemness and is a viable therapeutic target in acute myeloid leukemia, Journal of Experimental Medicine, 214 (2017) 359-380.

C. Riether, T. Pabst, S. Hopner, U. Bacher, M. Hinterbrandner, Y. Banz, R. Müller, M. G. Manz, W. H. Gharib, D. Francisco, Targeting CD70 with cusatuzumab eliminates acute myeloid leukemia stem cells in patients treated with hypomethylating agents, Nature medicine, 26 (2020) 1459-1467.

Gardai S J, McPhillips K A, Frasch S C, Janssen W J, Starefeldt A, Murphy-Ullrich J E, Bratton D L, Oldenborg P A, Michalak M, Henson P M. Cell-surface calreticulin initiates clearance of viable or apoptotic cells through trans-activation of LRP on the phagocyte. Cell. 2005; 123:321-334

Gennaro, ed., Remington: The Science and Practice of Pharmacy, 20th Ed., Lippincott Williams & Wilkins 2003

H. J. Gruss, M. E. Kadin, 2 Pathophysiology of Hodgkin's disease: functional and molecular aspects, Bailliére's clinical haematology, 9 (1996) 417-446.

J. A. McEarchern, L. M. Smith, C. F. McDonagh, K. Klussman, K. A. Gordon, C. A. Morris-Tilden, S. Duniho, M. Ryan, T. E. Boursalian, P. J. Carter, Preclinical characterization of SGN-70, a humanized antibody directed against CD70, Clinical Cancer Research, 14 (2008) 7763-7772.

J. Held-Feindt, R. Mentlein, CD70/CD27 ligand, a member of the TNF family, is expressed in human brain tumors, International journal of cancer, 98 (2002) 352-356.

J. H. Pahl, S. J. Santos, M. L. Kuijjer, G. H. Boerman, L. G. Sand, K. Szuhai, A. Cleton-Jansen, R. M. Egeler, J. V. Boveé, M. W. Schilham, Expression of the immune regulation antigen CD70 in osteosarcoma, Cancer cell international, 15 (2015) 1-9.

J. Jacobs, K. Zwaenepoel, C. Rolfo, J. Van den Bossche, C. Deben, K. Silence, C. Hermans, E. Smits, P. Van Schil, F. Lardon, Unlocking the potential of CD70 as a novel immunotherapeutic target for non-small cell lung cancer, Oncotarget, 6 (2015) 13462.

J. R. Robinson, ed., Sustained and Controlled Release Drug Delivery Systems, Marcel Dekker, Inc., New York, 1978

J. Wischhusen, G. Jung, I. Radovanovic, C. Beier, J. P. Steinbach, A. Rimner, H. Huang, J. B. Schulz, H. Ohgaki, A. Aguzzi, Identification of CD70-mediated apoptosis of immune effector cells as a novel immune escape pathway of human glioblastoma, Cancer research, 62 (2002) 2592-2599.

Lee W Y, Weber D A, Laur O, Severson E A, McCall I, Jen R P, Chin A C, Wu T, Gernert K M, Parkos C A. Novel Structural Determinants on SIRPα that Mediate Binding to CD47. J Immunol. 2007, 179:7741-7750

Lutfi F, Wu L, Sunshine S, Cao X. Targeting the CD27-CD70 Pathway to Improve Outcomes in Both Checkpoint Immunotherapy and Allogeneic Hematopoietic Cell Transplantation. Front Immunol. 2021 Sep. 22;

Obeid M, Panaretakis T, Joza N, Tufi R, Tesniere A, van Endert P, Zitvogel L, Kroemer G. Calreticulin exposure is required for the immunogenicity of gamma-irradiation and UVC lightinduced apoptosis. Cell Death Differ. 2007, 14:1848-1850

Orr A W, Pedraza C E, Pallero M A, Elzie C A, Goicoechea S, Strickland D K, Murphy-Ullrich J E. Low density lipoprotein receptor-related protein is a calreticulin coreceptor that signals focal adhesion disassembly. J Cell Biol. 2003, 161:1179-1189

S. Aggarwal, T. He, W. Fitzhugh, K. Rosenthal, B. Field, D. Mesmer, E. Joseloff, S. Ruben, P. Moore, Membrane proteomic analyses of ovarian cancer identifies the immune modulators CD70 and B7-H2 as candidate markers of cisplatin response, in, AACR, 2008.

Shields R L, Namenuk A K, Hong K, Meng Y G, Rae J, Briggs J, Xie D, Lai J, Stadlen A, Li B, Fox J A, Presta L G. High Resolution Mapping of the Binding Site on Human IgG1 for FcγRI, FcγRII, FcγRIII, and FcRn and Design of IgG1 Variants with Improved Binding to the FcgR. JBC. 2001, 276:6591-6604

S. M. Lens, P. Drillenburg, B. F. Den Drijver, G. Van Schijndel, S. T. Pals, R. A. Van Lier, M. H. Van Oers, Aberrant expression and reverse signalling of CD70 on malignant B cells, British journal of haematology, 106 (1999) 491-503.

T. Hishima, M. Fukayama, Y. Hayashi, T. Fujii, T. Ooba, N. Funata, M. Koike, CD70 expression in thymic carcinoma, The American journal of surgical pathology, 24 (2000) 742-746.

Vlahopoulos, S A. Aberrant control of NF-κB in cancer permits transcriptional and phenotypic plasticity, to curtail dependence on host tissue: molecular mode. Cancer biology & medicine. 2017, 14: 254-270

Shim H. Bispecific Antibodies and Antibody-Drug Conjugates for Cancer Therapy: Technological Considerations. Biomolecules. 2020 Feb. 26; 10(3):360

Wang S, Chen K, Lei Q, Ma P, Yuan A Q, Zhao Y, Jiang Y, Fang H, Xing S, Fang Y, Jiang N, Miao H, Zhang M, Sun S, Yu Z, Tao W, Zhu Q, Nie Y, Li N. The state of the art of bispecific antibodies for treating human malignancies. EMBO Mol Med. 2021 Aug. 24:e14291. doi: 10.15252/emmm.202114291

---

The invention claimed is:

1. An isolated monoclonal antibody or an antigen binding portion thereof, that binds CD70, comprising
   i) a heavy chain variable region, wherein the heavy chain variable region comprises a heavy chain variable region CDR-1 (HV-CDR1), a HV-CDR2 and a HV-CDR3 comprising the amino acid sequences set forth in SEQ ID NOs: 1, 2 and 3, respectively; and
   ii) a light chain variable region, wherein the light chain variable region comprises a light chain variable region CDR-1 (LV-CDR1), a LV-CDR2 and a LV-CDR3 comprising the amino acid sequences set forth in SEQ ID NOs: 4, 5 and 6, respectively.

2. The isolated monoclonal antibody or antigen binding portion thereof of claim 1, wherein the heavy chain variable region comprises an amino acid sequence having at least 90% or 95% identity to SEQ ID NOs: 7 or 9.

3. The isolated monoclonal antibody or antigen binding portion thereof of claim 1, wherein the light chain variable region comprises an amino acid sequence having at least 90% or 95% identity to SEQ ID NOs: 8 or 10 (X=N or X=E).

4. The isolated monoclonal antibody or antigen binding portion thereof of claim 2, wherein the heavy chain variable region and the light chain variable region comprise amino acid sequences having at least 90% or 95% identity to i) SEQ ID NOs: 7 and 8, respectively; ii) SEQ ID NOs: 9 and 10 (X=N), respectively; or iii) SEQ ID NOs: 9 and 10 (X=E), respectively.

5. The isolated monoclonal antibody or antigen binding portion thereof of claim 1, which is an IgG1, IgG2 or IgG4 isotype.

6. The isolated monoclonal antibody or antigen binding portion thereof of claim 1, comprising a heavy chain constant region and a light chain constant region having the amino acid sequences of SEQ ID NOs: 11 and 12, respectively.

7. The isolated monoclonal antibody or antigen binding portion thereof of claim 1, which is mouse, chimeric or humanized.

8. A nucleic acid molecule encoding the isolated monoclonal antibody or antigen binding portion thereof of claim 1.

9. An expression vector comprising the nucleic acid molecule of claim 8.

10. A host cell comprising the expression vector of claim 9.

11. A pharmaceutical composition comprising a therapeutically effective amount of the isolated monoclonal antibody or antigen binding portion thereof of claim 1, and a pharmaceutically acceptable carrier.

12. A method for treating a disease associated with CD70-CD27 signaling in a subject in need thereof, comprising administering to the subject the pharmaceutical composition of claim 11.

13. The method of claim 12, wherein the disease is a cancer or an inflammatory disease.

14. The method of claim 13, wherein the cancer is a solid cancer or a hematological cancer.

15. The method of claim 14, wherein the cancer is kidney cancer, myelodysplastic syndromes, cutaneous T-cell lymphomas, nasopharyngeal carcinoma, Epstein-Barr virus induced cancer, Hodgkin lymphoma (HL), non-Hodgkin lymphoma (NHL), diffuse large B cell lymphoma, follicular lymphoma, B lymphocytic leukemia, Burkitt lymphoma, multiple myeloma, Waldenstrom macroglobulinemia, thymic carcinoma, glioblastoma, brain cancer, osteosarcoma, melanoma, ovarian cancer, renal cell carcinoma, breast cancer, squamous cell carcinoma of the head and neck, colorectal cancer, mantle cell lymphoma, prostate adenocarcinoma, colorectal adenocarcinoma, lymphoma of the central nervous system, or non-small cell lung cancer.

16. The method of claim 13, wherein the inflammatory disease is arthritis, inflammatory bowel disease, or lupus.

* * * * *